(12) United States Patent
Kocis et al.

(10) Patent No.: US 9,679,341 B2
(45) Date of Patent: Jun. 13, 2017

(54) METHODS, SYSTEMS, AND COMPUTER READABLE MEDIA FOR EVALUATING A HOSPITAL PATIENT'S RISK OF MORTALITY

(71) Applicant: The University of North Carolina at Chapel Hill, Chapel Hill, NC (US)

(72) Inventors: Keith C. Kocis, Chapel Hill, NC (US); Daniel J. Kocis, Jr., Manorville, NY (US)

(73) Assignee: The University of North Carolina At Chapel Hill, Chapel Hill, NC (US)

( * ) Notice: Subject to any disclaimer, the term of this patent is extended or adjusted under 35 U.S.C. 154(b) by 863 days.

(21) Appl. No.: 13/721,010

(22) Filed: Dec. 19, 2012

(65) Prior Publication Data
US 2013/0197924 A1    Aug. 1, 2013

Related U.S. Application Data

(63) Continuation of application No. PCT/US2011/042416, filed on Jun. 29, 2011, which is a continuation-in-part of application No. 12/302,008, filed as application No. PCT/US2007/012736 on May 30, 2007.

(60) Provisional application No. 61/359,708, filed on Jun. 29, 2010, provisional application No. 60/809,283, filed on May 30, 2006.

(51) Int. Cl.
G06Q 50/22    (2012.01)
G06Q 50/24    (2012.01)
G06Q 10/10    (2012.01)
G06F 19/00    (2011.01)

(52) U.S. Cl.
CPC .......... *G06Q 50/22* (2013.01); *G06F 19/345* (2013.01); *G06F 19/3431* (2013.01); *G06Q 10/10* (2013.01)

(58) Field of Classification Search
CPC ......... G06Q 50/24; G06Q 50/22; G06Q 10/00
See application file for complete search history.

(56) References Cited

U.S. PATENT DOCUMENTS

2005/0234354 A1* 10/2005 Rowlandson ........ A61B 5/0452
                                                      600/509
2008/0091471 A1*  4/2008 Michon ............... G06F 19/3443
                                                        705/3

OTHER PUBLICATIONS

Notice of Allowance and Fee(s) Due for U.S. Appl. No. 12/302,008 (Jun. 20, 2014).

(Continued)

*Primary Examiner* — Maroun Kanaan
(74) *Attorney, Agent, or Firm* — K&L Gates LLP

(57) ABSTRACT

A method for evaluating a hospital patient's risk of mortality includes collecting data from physiologic signals generated by patient monitors, physiologic signals of organ function, and demographic information for a patient. A measure of the variability of at least one of the physiologic signals is determined. Data and the measure of variability are analyzed to determine whether a value for a particular physiologic or demographic variable falls within a critical interval for the variable that indicates that the value is predictive of mortality or survival. Each time a value for a physiological or demographic variable for the patient falls within a critical interval, the occurrence of an event for the patient is recorded. The number of events for the patient is counted over a time period. Output perceptible by human user that indicates the patient's risk of mortality or likelihood of survival is generated based on the count.

9 Claims, 32 Drawing Sheets

(56) References Cited

OTHER PUBLICATIONS

Non-Final Office Action for U.S. Appl. No. 12/302,008 (Dec. 5, 2013).
Final Office Action for U.S. Appl. No. 12/302,008 (Jan. 7, 2015).
Non-Final Office Action for U.S. Appl. No. 12/302,008 (Aug. 7, 2014).
Knaus et al., "The APACHE III prognostic system: Risk prediction of hospital mortality for critically ill hospitalized adults," Chest, 100, pp. 1619-1636 (1991).
Kruse et al., "Comparison of clinical assessment with APACHE II for predicting mortality risk in patients admitted to a medical intensive care unit," JAMA, 260(12), pp. 1739-1742 (1988).
Marcin et al., "Combining physician's subjective and physiology-based objective mortality risk predictions," Crit Care Med, 28(8), pp. 3113-3114 (2000).
Rocker et al., "Clinician predictions of intensive care unit mortality," Crit Care Med, 32(5), pp. 1149-1154 (2004).
Smith et al., "Hospital wide physiological surveillance—a new approach to the early identification and management of the sick patient," Resuscitation, 71(1), pp. 19-28 (Oct. 2006).
Tarassenko et al., "Integrated monitoring and analysis for early warning of patient deterioration," Br J Anaesth, 97, pp. 64-68 (2006).
Watkinson et al., "A randomized controlled trial of the effect of continuous electronic physiological monitoring on the adverse event rate in high risk medical and surgical patients," Anaesthesia 61, pp. 1031-1039 (2006).
Yien et al., "Spectral analysis of systemic arterial pressure and heart rate signals as a prognostic tool for the prediction of patient outcome in the intensive care unit," Crit Care Med, 25, pp. 258-266 (1997).

\* cited by examiner

DEAD PICU
THE MEANS PROCEDURE

| VARIABLE | MEAN | Std Dev | VARIANCE | MINIMUM | MAXIMUM | N |
|---|---|---|---|---|---|---|
| pnn50 | 0 | 0 | 0 | 0 | 0 | 105664 |
| pnn100 | 0 | 0 | 0 | 0 | 0 | 105664 |
| pnn200 | 0.0071923 | 0.0528221 | 0.0027902 | 0 | 0.9922780 | 105664 |
| pnn300 | 0.1080836 | 0.2913443 | 0.0848815 | 0 | 0.9937888 | 105664 |
| pnn400 | 0.3028720 | 0.4268584 | 0.1822081 | 0 | 0.9935897 | 105664 |
| pnn500 | 0.3405127 | 0.4214867 | 0.1776511 | 0 | 0.9934211 | 105664 |
| pnn600 | 0.1618855 | 0.3109868 | 0.0967128 | 0 | 0.9934211 | 105664 |
| pnn700 | 0.0234902 | 0.1100181 | 0.0121040 | 0 | 0.9923077 | 105664 |
| pnn800 | 0.0153742 | 0.0767250 | 0.0058867 | 0 | 0.9923077 | 105664 |
| pnn900 | 0.0084066 | 0.0456894 | 0.0020875 | 0 | 0.9534884 | 105664 |
| pnn1000 | 0.0057024 | 0.0335443 | 0.0011252 | 0 | 0.7224490 | 105664 |
| pnn1000o | 0.0173942 | 0.0710719 | 0.0050512 | 0 | 0.9840000 | 105664 |

*FIG. 5A*

LIVE PICU
THE MEANS PROCEDURE

| VARIABLE | MEAN | Std Dev | VARIANCE | MINIMUM | MAXIMUM | N |
|---|---|---|---|---|---|---|
| pnn50 | 6.1405662E-9 | 4.9759771E-6 | 2.476035E-11 | 0 | 0.0040323 | 656659 |
| pnn100 | 0.000018966 | 0.0036391 | 0.000013243 | 0 | 0.7142857 | 656659 |
| pnn200 | 0.000500129 | 0.0192136 | 0.000363164 | 0 | 0.9922481 | 656659 |
| pnn300 | 0.0049646 | 0.0600159 | 0.0036019 | 0 | 0.9939394 | 656659 |
| pnn400 | 0.1388401 | 0.3025583 | 0.0915415 | 0 | 0.9939759 | 656659 |
| pnn500 | 0.3566494 | 0.4133237 | 0.1708365 | 0 | 0.9934211 | 656659 |
| pnn600 | 0.2273262 | 0.3440774 | 0.1183802 | 0 | 0.9930556 | 656659 |
| pnn700 | 0.1223216 | 0.2496523 | 0.0623263 | 0 | 0.9926471 | 656659 |
| pnn800 | 0.0629374 | 0.1584039 | 0.0250918 | 0 | 0.9923077 | 656659 |
| pnn900 | 0.0326490 | 0.0938397 | 0.0083059 | 0 | 0.9922481 | 656659 |
| pnn1000 | 0.0135719 | 0.0488648 | 0.0023875 | 0 | 0.9397590 | 656659 |
| pnn1000o | 0.0235014 | 0.0863901 | 0.0074632 | 0 | 0.9920000 | 656659 |

*FIG. 5B*

DEAD PICU
THE MEANS PROCEDURE

| VARIABLE | MEAN | Std Dev | VARIANCE | MINIMUM | MAXIMUM | N |
|---|---|---|---|---|---|---|
| RATIO | 0.5475689 | 0.3979583 | 0.1583708 | 0.038972 | 10.8972262 | 105664 |
| ULF | 9.7039194E-6 | 0.000281968 | 7.950572E-8 | 1.715726E-10 | 0.0540024 | 105664 |
| VLF | 0.000890117 | 0.0329209 | 0.0010838 | 1.3612728E-6 | 6.8905225 | 105664 |
| LF | 0.0020710 | 0.0785836 | 0.0061754 | 3.1578073-6 | 17.5578519 | 105664 |
| HF | 0.0032880 | 0.0202568 | 0.000410338 | 0 | 4.3284978 | 105664 |
| VHF | 0.0054152 | 0.0114744 | 0.000131661 | 0 | 1.5805266 | 105664 |

FIG. 6A

LIVE PICU
THE MEANS PROCEDURE

| VARIABLE | MEAN | Std Dev | VARIANCE | MINIMUM | MAXIMUM | N |
|---|---|---|---|---|---|---|
| RATIO | 0.8650416 | 3.3508340 | 11.2280887 | 0.0336705 | 705.7305467 | 656659 |
| ULF | 0.000056382 | 0.0056345 | 0.000031748 | 7.6014E-10 | 4.3003126 | 656659 |
| VLF | 0.0035131 | 0.2877154 | 0.0827801 | 1.7601426E-6 | 190.5933976 | 656659 |
| LF | 0.0044045 | 0.1710344 | 0.0292528 | 0.000014352 | 58.6030532 | 656659 |
| HF | 0.0044401 | 0.0888781 | 0.0078638 | 0 | 50.0547221 | 656659 |
| VHF | 0.0047622 | 0.0447621 | 0.0020036 | 0 | 28.7881662 | 656659 |

FIG. 6B

| ENTER VAL | RANGE | PICU COUNT | DEAD COUNT | INDEX | Prob | LEFT Conf | MORTALITY RATE | RIGHT Conf | SELECT |
|---|---|---|---|---|---|---|---|---|---|
| 1 | 0.03367047-0.34640151 | 76,241 | 36,311 | 344 | 0.000 | 47.27 | 47.63 | 47.98 | HIGH |
| 2 | 0.346402112-0.439258343 | 76,232 | 15,652 | 148 | 0.000 | 20.25 | 20.53 | 20.82 | HIGH |
| 3 | 0.439258833-0.49648596 | 76,232 | 12,479 | 118 | 0.000 | 16.11 | 16.37 | 16.63 | FLAT |
| 4 | 0.49648620-0.544375899 | 76,232 | 8,037 | 85 | 0.000 | 11.50 | 11.72 | 11.95 | FLAT |
| 5 | 0.544377051-0.612521286 | 76,232 | 6,506 | 62 | 0.000 | 8.34 | 8.53 | 8.73 | LOW |
| 6 | 0.61252217-0.715749856 | 76,232 | 5,249 | 50 | 0.000 | 6.71 | 6.89 | 7.07 | LOW |
| 7 | 0.715750008-0.861432643 | 77,465 | 5,275 | 49 | 0.000 | 6.63 | 6.81 | 6.99 | LOW |
| 8 | 0.861448546-1.119730555 | 76,233 | 5,878 | 56 | 0.000 | 7.52 | 7.71 | 7.90 | LOW |
| 9 | 1.119748978-1.499777383 | 76,233 | 5,397 | 56 | 0.000 | 7.55 | 7.71 | 7.93 | LOW |
| 10 | 1.499780634-795.7395467 | 74,991 | 3,480 | 33 | 0.000 | 4.49 | 44.6 | 4.79 | LOW |

FIG. 7

DEAD PICU
THE MEANS PROCEDURE

| VARIABLE | MEAN | Std Dev | VARIANCE | MINIMUM | MAXIMUM | N |
|---|---|---|---|---|---|---|
| RATIO | 0.5475689 | 0.3979583 | 0.1583708 | 0.0381972 | 10.8972262 | 105664 |
| RATIO_CMOVAV | 0.5475493 | 0.2778088 | 0.0771777 | 0.1291440 | 2.6945082 | 105664 |
| RATIO_CMOVSTD | 0.2124678 | 0.1931013 | 0.0372881 | -1.73472E-18 | 3.8410779 | 105664 |
| DERIV1_RATIO | 9.6549427E-8 | 0.0023481 | 5.5135594E-6 | -0.0551619 | 0.0559047 | 105664 |
| DERIV1_RATIO_CMOVAV | 6.6880406E-8 | 0.000063608 | 4.0459309E-9 | -0.0015887 | 0.0015779 | 105664 |
| DERIV1_RATIO_CMOVSTD | 0.0018233 | 0.0015016 | 2.2547139E-6 | -1.43821E-93 | 0.0120505 | 105664 |
| DERIV2_RATIO | -5.297347E-9 | 0.000028850 | 8.3234E-10 | -0.0012118 | 0.000904234 | 105664 |
| DERIV2_RATIO_CMOVAV | -3.199729E-9 | 9.2077017E-7 | 8.478177E-13 | -0.000035571 | 0.000028564 | 105664 |
| DERIV2_RATIO_CMOVSTD | 0.000022039 | 0.000018609 | 3.463014E-10 | -1.43821E-93 | 0.000226397 | 105664 |

*FIG. 8A*

LIVE PICU
THE MEANS PROCEDURE

| VARIABLE | MEAN | Std Dev | VARIANCE | MINIMUM | MAXIMUM | N |
|---|---|---|---|---|---|---|
| RATIO | 0.8650416 | 3.3508340 | 11.2280887 | 0.0336705 | 795.7395467 | 656659 |
| RATIO_CMOVAV | 0.8648648 | 1.4305640 | 2.0465134 | 0.1772132 | 147.5979595 | 656659 |
| RATIO_CMOVSTD | 0.3853615 | 3.0298718 | 9.1801231 | -4.85723E-17 | 310.3030093 | 656659 |
| DERIV1_RATIO | 3.7340002E-7 | 0.0114227 | 0.000130479 | -4.1634044 | 4.2015571 | 656659 |
| DERIV1_RATIO_CMOVAV | 3.1721199E-7 | 0.000654915 | 4.289138E-7 | -0.1252407 | 0.1252371 | 656659 |
| DERIV1_RATIO_CMOVSTD | 0.0028854 | 0.0111235 | 0.000123732 | -3.35583E-93 | 1.303643 | 656659 |
| DERIV2_RATIO | 4.5103394E-9 | 0.000118886 | 1.4133862E-8 | -0.0384450 | 0.0384463 | 656659 |
| DERIV2_RATIO_CMOVAV | 3.7799388E-9 | 2.6787591E-6 | 7.17575E-12 | -0.000797139 | 0.000797070 | 656659 |
| DERIV2_RATIO_CMOVSTD | 0.000034288 | 0.000114582 | 1.3129015E-8 | -3.35583E-93 | 0.0115419 | 656659 |

*FIG. 8B*

| ABSOLUTE_NEUT_CT | FIBRINDGEN-F1 | O2 SATURATION | PT |
|---|---|---|---|
| ALT | CGT | O2 SATURATION-VEN | PTH |
| APTT | GLUCOSE POC | PCO2 | SODIUM |
| AST | GLUCOSE RANDOM | PCO2/POC | SODIUM (BG/CC) |
| BASE BALANCE | GLUCOSE WHL BLOOD | PCO2-VENOUS | SODIUM-BG/POC |
| BASE BALANCE/POC | GLUCOSE-BG/POC | PCO2-VENOUS/POC | TROPONIN T |
| BASE BALANCE-VEN | HEMATOCRIT | PH | UREA NITROGEN |
| BASE BALANCE-VENOUS/POC | HEMATOCRIT-BG/P | PH/POC | URIC ACID |
| BICARB/POC | HEMOGLOBIN | PHOSPHORUS | WBC |
| BICARBONATE | HEMOGLOBIN(BG/CC) | PH-VENOUS | |
| BICARBONATE-VEN | INR | PH-VENOUS/POC | |
| BICARB-VEN/POC | IONIZED CA VENOUS | PLATELET COUNT | |
| BILIRUBIN TOTAL | IONIZED CA-SG/POC | PO2 | |
| CALCIUM | IONIZED CALCIUM | PO2/POC | |
| CHLORIDE | LACTATE ARTERIAL | PO2-VENOUS | |
| CK-MB | LACTATE VENOUS | PO2-VENOUS/POC | |
| CO2 | LACTATE-PCC | POTASSIUM | |
| CREATINE KINASE | LACTATE-VEN/POC | POTASSIUM (BG/CC) | |
| CREATININE | MAGNESIUM | POTASSIUM-BG/POC | |
| D-DIMER QUANT | NEUT LEFT SHIFT | PROTEIN TOTAL | |

FIG. 9A

| ART DIAS | SPO2 |
|---|---|
| ART MEAN | SpO2 PULSE RATE |
| ART PULSE RATE | TEMP 2 |
| ART SYS | TEMPERATURE |
| CAPNO RESP RATE | UA DIAS |
| CORE TEMP | UA MEAN |
| CVP | UA SYS |
| ETCO2 | UAP PULSE RATE |
| HEART RATE | UV DIAS |
| HR ECG 2 | UV SYS |
| ICP | UVP MEAN |
| MAP | |
| NIBP DICS | |
| NIBP MEAN | |
| NIBP SYS | |
| RESP RATE | |

FIG. 9B

| QTMS 4.0 | SINGLE FACTOR SCAN SUMMARY TABLE OF PROJECT TESTRUN THE VARIABLES ARE LISTED IN ALPHABETICAL ORDER | | | | | | |
|---|---|---|---|---|---|---|---|
| # | VARIABLE | NO. OF INTERVALS | CHI-SQUARE | CHI-SQ. PROB. | T. TEST | T. TEST PROB. | MEAN OF NON.RESP. | MEAN OF RESPONDERS |
| 1 | ABSOLUTE_NEUT_CUT | 10 | 101786.26 | 0.0000 | -68.0354 | 0.0000 | 7.746 | 10.525 |
| 2 | ABSOLUTE_NEUT_CUT_CMOVAV | 10 | 169838.31 | 0.0000 | -114.3353 | 0.0000 | 6.767 | 10.967 |
| 3 | ABSOLUTE_NEUT_CUT_CMOVSTD | 10 | 135636.67 | 0.0000 | -87.2072 | 0.0000 | 3.128 | 4.488 |
| 4 | ALT | 10 | 67695.334 | 0.0000 | -18.6174 | 0.0000 | 123.138 | 139.497 |
| 5 | ALT_CMOVAV | 10 | 127890.70 | 0.0000 | -101.9348 | 0.0000 | 100.744 | 175.135 |
| 6 | ALT_CMOVSTD | 10 | 86256.561 | 0.0000 | -57.7809 | 0.0000 | 65.323 | 98.400 |
| 7 | ANDMOL | 2 | 2.356 | 0.1248 | 4.1232 | 0.0000 | 0.000 | 0.000 |
| 8 | APTT | 10 | 149982.52 | 0.0000 | -59.7890 | 0.0000 | 38.881 | 46.767 |
| 9 | APTT_CMOVAV | 10 | 183124.95 | 0.0000 | -55.6134 | 0.0000 | 43.090 | 49.290 |
| 10 | APTT_CMOVSTD | 10 | 183231.68 | 0.0000 | -25.1562 | 0.0000 | 12.151 | 13.995 |
| 11 | AST | 8 | 76281.535 | 0.0000 | -50.7186 | 0.0000 | 221.533 | 457.244 |
| 12 | AST_CMOVAV | 8 | 59752.489 | 0.0000 | -74.5702 | 0.0000 | 135.681 | 469.084 |
| 13 | AST_CMOVSTD | 8 | 75688.803 | 0.0000 | -133.3939 | 0.0000 | 110.280 | 218.933 |
| 14 | BILIRUBIN_TOTAL | 8 | 118250.25 | 0.0000 | -92.4685 | 0.0000 | 0.720 | 1.696 |
| 15 | BILIRUBIN_TOTAL_CMOVAV | 8 | 159809.90 | 0.0000 | -210.8066 | 0.0000 | 0.662 | 2.390 |
| 16 | BILIRUBIN_TOTAL_CMOVSTD | 7 | 166362.96 | 0.0000 | -252.6595 | 0.0000 | 0.205 | 2.029 |
| 17 | CALCIUM | 10 | 61034.470 | 0.0000 | 55.1787 | 0.0000 | 9.091 | 8.898 |
| 18 | CALCIUM_CMOVAV | 10 | 104352.22 | 0.0000 | 139.5541 | 0.0000 | 9.119 | 8.849 |
| 19 | CMOVAV_CMOVSTD | 10 | 72683.616 | 0.0000 | 22.0857 | 0.0000 | 0.644 | 0.615 |
| 20 | CAPNO_RESP_RATE | 10 | 45764.334 | 0.0000 | -11.3172 | 0.0000 | 24.588 | 25.261 |
| 21 | CAPNO_RESP_RATE_CMOVAV | 10 | 44966.418 | 0.0000 | -9.9354 | 0.0000 | 25.023 | 25.560 |
| 22 | CAPNO_RESP_RATE_CMOVSTD | 10 | 48770.078 | 0.0000 | 104.1389 | 0.0000 | 3.229 | 1.585 |
| 23 | CHLORIDE | 9 | 66526.244 | 0.0000 | 1.4763 | 0.1399 | 102.394 | 102.342 |
| 24 | CHLORIDE_CMOVAV | 10 | 93255.426 | 0.0000 | 9.8423 | 0.0000 | 102.143 | 101.887 |
| 25 | CHLORIDE_CMOVSTD | 10 | 65547.947 | 0.0000 | -1.4849 | 0.1376 | 4.790 | 4.801 |
| 26 | CO2 | 9 | 55048.530 | 0.0000 | 31.8660 | 0.0000 | 24.945 | 24.368 |
| 27 | CO2_CMOVAV | 10 | 138557.64 | 0.0000 | 32.0350 | 0.0000 | 24.862 | 24.481 |
| 28 | CO2_CMOVSTD | 10 | 78498.570 | 0.0000 | -0.0665 | 0.9470 | 3.602 | 3.602 |
| 29 | CREATININE | 10 | 207820.93 | 0.0000 | -203.0302 | 0.0000 | 0.536 | 1.747 |
| 30 | CREATININE_CMOVAV | 10 | 233789.80 | 0.0000 | -231.1729 | 0.0000 | 0.530 | 1.821 |
| 31 | CREATININE_CMOVSTD | 10 | 263725.30 | 0.0000 | -213.6878 | 0.0000 | 0.110 | 0.545 |
| 32 | CVP | 10 | 121734.85 | 0.0000 | -99.7933 | 0.0000 | 18.407 | 44.714 |
| 33 | CVP_CMOVAV | 10 | 137075.09 | 0.0000 | -116.0867 | 0.0000 | 18.119 | 47.277 |
| 34 | CVP_CMOVSTD | 10 | 47521.818 | 0.0000 | -73.8026 | 0.0000 | 6.298 | 13.571 |
| 35 | DERIV1_ABSOLUTE_NEUT_CT | 10 | 63174.243 | 0.0000 | 12.0163 | 0.0000 | 0.000 | 0.000 |
| 36 | DERIV1_ABSOLUTE_NEUT_CT_CMOVAV | 10 | 48955.497 | 0.0000 | 58.8763 | 0.0000 | 0.000 | 0.000 |
| 37 | DERIV1_ABSOLUTE_NEUT_CT_CMOVSTD | 10 | 92626.641 | 0.0000 | 88.6559 | 0.0000 | 0.000 | 0.000 |
| 38 | DERIV1_ALT | 10 | 76121.510 | 0.0000 | 37.4061 | 0.0000 | 0.000 | -0.000 |
| 39 | DERIV1_ALT_CMOVAV | 10 | 116295.81 | 0.0000 | -125.2304 | 0.0000 | 0.000 | 0.013 |
| 40 | DERIV1_ALT_CMOVSTD | 10 | 141896.62 | 0.0000 | -121.4974 | 0.0000 | 0.003 | 0.054 |
| 41 | DERIV1_APTT | 9 | 123445.00 | 0.0000 | 13.7649 | 0.0000 | 0.000 | -0.000 |

*FIG. 10A*

| QTMS 4.0 | SINGLE FACTOR SCAN SUMMARY TABLE OF PROJECT TESTRUN THE VARIABLES ARE LISTED IN ALPHABETICAL ORDER | | | | | | | |
|---|---|---|---|---|---|---|---|---|
| # | VARIABLE | NO. OF INTERVALS | CHI-SQUARE | CHI-SQ. PROB. | T. TEST | T. TEST PROB. | MEAN OF NON.RESP. | MEAN OF RESPONDERS |
| 452 | PLATELET_COUNT_CMOVAV | 10 | 202640.10 | 0.0000 | 294.3285 | 0.0000 | 342.245 | 169.428 |
| 453 | PLATELET_COUNT_CMOVSTD | 10 | 119631.52 | 0.0000 | 256.7107 | 0.0000 | 114.839 | 60.510 |
| 454 | PNN1000 | 3 | 5189.494 | 0.0000 | 65.8434 | 0.0000 | 0.014 | 0.006 |
| 455 | PNN1000P | 4 | 6197.004 | 0.0000 | 25.1068 | 0.0000 | 0.024 | 0.017 |
| 456 | PNN200 | 2 | 20604.205 | 0.0000 | -40.7510 | 0.0000 | 0.001 | 0.007 |
| 457 | PNN300 | 2 | 30763.744 | 0.0000 | -114.6616 | 0.0000 | 0.005 | 0.108 |
| 458 | PNN400 | 5 | 21781.124 | 0.0000 | -120.1509 | 0.0000 | 0.139 | 0.303 |
| 459 | PNN500 | 7 | 8773.508 | 0.0000 | 11.5811 | 0.0000 | 0.357 | 0.341 |
| 460 | PNN600 | 7 | 10369.983 | 0.0000 | 62.5211 | 0.0000 | 0.227 | 0.162 |
| 461 | PNN700 | 6 | 21305.207 | 0.0000 | 215.9426 | 0.0000 | 0.122 | 0.023 |
| 462 | PNN800 | 5 | 15442.091 | 0.0000 | 155.1976 | 0.0000 | 0.063 | 0.015 |
| 463 | PNN900 | 4 | 12129.250 | 0.0000 | 133.1152 | 0.0000 | 0.033 | 0.008 |
| 464 | PROTEIN_TOTAL | 8 | 72238.869 | 0.0000 | -108.0584 | 0.0000 | 5.147 | 5.832 |
| 465 | PROTEIN_TOTAL_CMOVAV | 8 | 67751.460 | 0.0000 | -45.6411 | 0.0000 | 5.465 | 5.678 |
| 466 | PROTEIN_TOTAL_CMOVSTD | 8 | 169068.31 | 0.0000 | 304.3326 | 0.0000 | 0.827 | 0.439 |
| 467 | RATIO | 10 | 81516.074 | 0.0000 | 73.6169 | 0.0000 | 0.865 | 0.548 |
| 468 | RATIO_CMOVAV | 10 | 144548.40 | 0.0000 | 161.7828 | 0.0000 | 0.865 | 0.548 |
| 469 | RATIO_CMOVSTD | 10 | 46899.538 | 0.0000 | 45.6680 | 0.0000 | 0.385 | 0.212 |
| 470 | RESP_RATE | 10 | 5679.399 | 0.0000 | -35.8331 | 0.0000 | 29.038 | 31.892 |
| 471 | RESP_RATE_CMOVAV | 10 | 5964.430 | 0.0000 | -40.9464 | 0.0000 | 28.881 | 31.702 |
| 472 | RESP_RATE_CMOVSTD | 10 | 5824.999 | 0.0000 | -11.7409 | 0.0000 | 8.015 | 8.414 |
| 473 | SPO2 | 9 | 84339.963 | 0.0000 | 234.2704 | 0.0000 | 96.474 | 89.999 |
| 474 | SPO2_CMOVAV | 10 | 103215.50 | 0.0000 | 261.4152 | 0.0000 | 96.594 | 90.052 |
| 475 | SPO2_CMOVSTD | 10 | 5703.834 | 0.0000 | -17.9558 | 0.0000 | 2.272 | 2.436 |
| 476 | SPO2_PULSE_RATE | 10 | 35957.376 | 0.0000 | -208.0506 | 0.0000 | 119.222 | 136.360 |
| 477 | SPO2_PULSE_RATE_CMOVAV | 10 | 44546.210 | 0.0000 | -226.3475 | 0.0000 | 119.356 | 136.539 |
| 478 | SPO2_PULSE_RATE_CMOVSTD | 10 | 64473.674 | 0.0000 | 175.6956 | 0.0000 | 10.344 | 5.693 |
| 479 | TEMPERATURE | 9 | 31893.416 | 0.0000 | 62.0223 | 0.0000 | 37.184 | 36.052 |
| 480 | TEMPERATURE_CMOVAV | 10 | 34350.914 | 0.0000 | 58.2470 | 0.0000 | 37.224 | 36.682 |
| 481 | TEMPERATURE_CMOVSTD | 10 | 26665.736 | 0.0000 | -59.3761 | 0.0000 | 0.298 | 1.000 |
| 482 | TROPONIN_T | 5 | 1190.672 | 0.0000 | -673.6947 | 0.0000 | 0.328 | 3.955 |
| 483 | TROPONIN_T_CMOVAV | 5 | 1190.672 | 0.0000 | -1638.000 | 0.0000 | 0.303 | 4.437 |
| 484 | TROPONIN_T_CMOVSTD | 4 | 1183.480 | 0.0000 | -175.9527 | 0.0000 | 0.099 | 0.683 |
| 485 | ULF | 10 | 96956.433 | 0.0000 | 6.6616 | 0.0000 | 0.000 | 0.000 |
| 486 | UREA_NITROGEN | 9 | 224418.18 | 0.0000 | -245.6581 | 0.0000 | 13.822 | 49.128 |
| 487 | UREA_NITROGEN_CMOVAV | 10 | 230750.41 | 0.0000 | -265.8944 | 0.0000 | 13.755 | 50.140 |
| 488 | UREA_NITROGEN_CMOVSTD | 10 | 250838.84 | 0.0000 | -300.7299 | 0.0000 | 5.925 | 14.020 |
| 489 | URIC_ACID | 5 | 61063.624 | 0.0000 | 497.8559 | 0.0000 | 3.985 | 1.097 |
| 490 | URIC_ACID_CMOVAV | 5 | 48697.756 | 0.0000 | 220.6708 | 0.0000 | 3.519 | 2.798 |
| 491 | URIC_ACID_CMOVSTD | 5 | 54898.675 | 0.0000 | -132.1616 | 0.0000 | 1.063 | 1.486 |
| 492 | VHF | 10 | 20886.701 | 0.0000 | -9.9617 | 0.0000 | 0.005 | 0.005 |

*FIG. 10B*

| QTMS 4.0 | INTERVALS AND THEIR CODED VARIABLES OF PROJECT TESTRUN THAT HAVE -MORTAL- RATES SIGNIFICANTLY HIGHER (WITH 95% CONFIDENCE) THAN THE OVERAL -MORTAL- RATE + 20% | | | | | | |
|---|---|---|---|---|---|---|---|
| NEW, CODED VARIABLE | ORIGINAL VARIABLE | INTERVAL | NO. OF PATIENTS- | NO. OF DEADS. | -MORAL- RATE | -MORAL- INDEX | CONF. INDEX |
| CODED1 | UREA_NITROGEN_CMOVSTD | 16.39657339 - 27.47294123 | 35757 | 35757 | 100.00 | 721 | 721 |
| CODED2 | GGT_CMOVAV | 243.375 - 386 | 19490 | 19490 | 100.00 | 721 | 721 |
| CODED3 | DERIV1_FIBRINOGEN_F_I_CMOVAV | -0.00001388 - 0.000138223 | 15968 | 15968 | 100.00 | 721 | 721 |
| CODED4 | D_DIMER_QUANT_CMOVSTD | 2070.603068 - 6380.224487 | 15234 | 15234 | 100.00 | 721 | 721 |
| CODED5 | BILIRUBIN_TOTAL_CMOVSTD | 1.935597052 - 4.652239604 | 13845 | 13845 | 100.00 | 721 | 721 |
| CODED6 | DERIV1_FIBRINOGEN_F_I_CMOVSTD | 0 | 13565 | 13565 | 100.00 | 721 | 721 |
| CODED7 | DERIV2_FIBRINOGEN_F_I_CMOVAV | 0 | 13565 | 13565 | 100.00 | 721 | 721 |
| CODED8 | D_DIMER_QUANT_CMOVAV | 5323.5 | 13565 | 13565 | 100.00 | 721 | 721 |
| CODED9 | DERIV2_GGT_CMOVSTD | 7.806672E-9 - 1.147579E-8 | 13133 | 13133 | 100.00 | 721 | 721 |
| CODED10 | DERIV1_ALT_CMOVSTD | 0.169115568 - 0.188612207 | 11552 | 11552 | 100.00 | 721 | 721 |
| CODED11 | DERIV1_BILIRUBIN_TOTAL_CMOVSTD | 0.000476013 - 0.000508497 | 9479 | 9479 | 100.00 | 721 | 721 |
| CODED12 | DERIV1_ALT_CMOVAV | 0.039836229 - 0.047007196 | 9007 | 9007 | 100.00 | 721 | 721 |
| CODED13 | DERIV2_D_DIMER_QUANT_CMOVSTD | 8.892813E-7 - 1.061478E-6 | 7051 | 7051 | 100.00 | 721 | 721 |
| CODED14 | DERIV1_AST_CMOVAV | 0.0375103 - 0.041215289 | 7017 | 7017 | 100.00 | 721 | 721 |
| CODED15 | DERIV1_AST_CMOVSTD | 0.15921377 - 0.166908355 | 7017 | 7017 | 100.00 | 721 | 721 |
| CODED16 | DERIV1_URIC_ACID | 0.343344E-7 | 7017 | 7017 | 100.00 | 721 | 721 |
| CODED17 | DERIV1_URIC_ACID_CMOVSTD | 3.990617E-6 | 7017 | 7017 | 100.00 | 721 | 721 |
| CODED18 | DERIV2_URIC_ACID_CMOVAV | 4.79692E-12 | 7017 | 7017 | 100.00 | 721 | 721 |
| CODED19 | DERIV2_URIC_ACID_CMOVSTD | 1.01064E-11 | 7017 | 7017 | 100.00 | 721 | 721 |
| CODED20 | URIC_ACID | 0.9 | 7017 | 7017 | 100.00 | 721 | 721 |
| CODED21 | DERIV1_FIBRINOGEN_F_I_CMOVAV | -0.00010762 - -0.0000397 | 6037 | 6037 | 100.00 | 721 | 721 |
| CODED22 | DERIV1_FIBRINOGEN_F_I_CMOVSTD | 0.000764479 - 0.000781514 | 5979 | 5979 | 100.00 | 721 | 721 |
| CODED23 | D_DIMER_QUANT_CMOVSTD | 1026.01194 - 2004.861061 | 5293 | 5293 | 100.00 | 721 | 721 |
| CODED24 | AST_CMOVAV | 589.1818182 - 3027 | 4392 | 4392 | 100.00 | 721 | 721 |
| CODED25 | DERIV1_D_DIMER_QUANT_CMOVAV | 0.006040644 | 4160 | 4160 | 100.00 | 721 | 721 |
| CODED26 | DERIV1_D_DIMER_QUANT_CMOVSTD | 0.035055847 | 4160 | 4160 | 100.00 | 721 | 721 |
| CODED27 | DERIV2_FIBRINOGEN_F_I_CMOVAV | 3.694288E-8 | 4160 | 4160 | 100.00 | 721 | 721 |
| CODED28 | FIBRINOGEN_F_I_CMOVAV | 176.7142857 | 4160 | 4160 | 100.00 | 721 | 721 |
| CODED29 | DERIV2_FIBRINOGEN_F_I | 2.71389E-10 - 4.955707E-9 | 3963 | 3963 | 100.00 | 721 | 721 |
| CODED30 | DERIV2_D_DIMER_QUANT_CMOVAV | -1.98988E-7 - -4.34546E-8 | 3697 | 3697 | 100.00 | 721 | 721 |
| CODED31 | D_DIMER_QUANT_CMOVAV | 4069.692308 - 4967 | 3402 | 3402 | 100.00 | 721 | 721 |
| CODED32 | DERIV2_FIBRINOGEN_F_I_CMOVAV | 1.616511E-9 - 4.955707E-9 | 3209 | 3209 | 100.00 | 721 | 721 |
| CODED33 | DERIV1_FIBRINOGEN_F_I | 0.000150946 - 0.00043882 | 3148 | 3148 | 100.00 | 721 | 721 |
| CODED34 | ABSOLUTE_NEUT_CT_CMOVAV | 22.125 - 22.6 | 2910 | 2910 | 100.00 | 721 | 721 |
| CODED35 | DERIV1_BILIRUBIN_TOTAL_CMOVAV | 0.000119513 - 0.000125036 | 2760 | 2760 | 100.00 | 721 | 721 |
| CODED36 | DERIV2_BILIRUBIN_TOTAL_CMOVSTD | 9.679595E-9 - 9.902011E-9 | 2760 | 2760 | 100.00 | 721 | 721 |
| CODED37 | AST | 2811 - 2860 | 2195 | 2195 | 100.00 | 721 | 721 |
| CODED38 | DERIV2_AST_CMOVSTD | 3.286978E-6 | 1265 | 1265 | 100.00 | 721 | 721 |
| CODED39 | DERIV1_TROPONIN_T | 0.000039239 | 207 | 207 | 100.00 | 721 | 721 |
| CODED40 | DERIV1_TROPONIN_T_CMOVAV | 0.000039239 | 207 | 207 | 100.00 | 721 | 721 |
| CODED41 | DERIV1_TROPONIN_T_CMOVSTD | 0 | 207 | 207 | 100.00 | 721 | 721 |
| CODED42 | DERIV2_TROPONIN_T | 0 | 207 | 207 | 100.00 | 721 | 721 |
| CODED43 | DERIV2_TROPONIN_T_CMOVAV | 0 | 207 | 207 | 100.00 | 721 | 721 |

*FIG. 11A*

| QTMS 4.0 | INTERVALS AND THEIR CODED VARIABLES OF PROJECT TESTRUN THAT HAVE -MORTAL- RATES SIGNIFICANTLY HIGHER (WITH 95% CONFIDENCE) THAN THE OVERAL -MORTAL- RATE + 20% | | | | | | |
|---|---|---|---|---|---|---|---|
| NEW, CODED VARIABLE | ORIGINAL VARIABLE | INTERVAL | NO. OF PATIENTS- | NO. OF DEADS. | -MORAL- RATE | -MORAL- INDEX | CONF. INDEX |
| CODED2366 | DERIV2_MULTI_HEMA | -8.0141E-10 - -2.9432E-10 | 39920 | 6915 | 17.32 | 125 | 122 |
| CODED2367 | RESP_RATE | 47.6779661 - 199.1208054 | 69841 | 12026 | 17.22 | 124 | 122 |
| CODED2368 | DERIV2_MULTI_PCO2_VEN_CMOVAV | -7.60128E-9 - -2.9522E-9 | 23376 | 4073 | 17.42 | 126 | 122 |
| CODED2369 | DERIV2_UREA_NITROGEN_CMOVSTD | 5.88583E-10 - 9.20105E-10 | 40019 | 6925 | 17.30 | 125 | 122 |
| CODED2370 | MULTI_BASE_CMOVSTD | 4.122256279 - 4.555373593 | 33774 | 5853 | 17.33 | 125 | 122 |
| CODED2371 | DERIV2_PHOSPHORUS | -1.5461E-10 - -6.4608E-11 | 39303 | 6796 | 17.29 | 125 | 122 |
| CODED2372 | DERIV2_PLATELET_COUNT_CMOVSTD | 9.06034E-8 - 1.924971E-7 | 38902 | 6722 | 17.28 | 125 | 122 |
| CODED2373 | TEMPERATURE | 38.50048732 - 73.48275862 | 10510 | 1853 | 17.63 | 127 | 122 |
| CODED2374 | DERIV1_MULTI_PO2_VEN | -0.00006551 - -1.12177E-6 | 23935 | 4156 | 17.36 | 125 | 122 |
| CODED2375 | MULTI_PCO2_VEN_CMOVSTD | 10.95445115 - 13.83032096 | 23482 | 4078 | 17.37 | 125 | 122 |
| CODED2376 | PHOSPHORUS | 5.7 - 6.1 | 46887 | 8071 | 17.21 | 124 | 122 |
| CODED2377 | MULTI_PCO2 | 18 - 37 | 25502 | 4421 | 17.34 | 125 | 122 |
| CODED2378 | DERIV1_MULTI_ART_CMOVAV | 0.010179604 - 0.490510929 | 23861 | 4140 | 17.35 | 125 | 122 |
| CODED2379 | NIBP_SYS_CMOVAV | 81.00053763 - 88.13232323 | 71684 | 12285 | 17.14 | 124 | 122 |
| CODED2380 | DERIV1_RATIO_CMOVAV | 0.0000E-309 - 9.001911E-6 | 76232 | 13058 | 17.13 | 124 | 122 |
| CODED2381 | SPO2_PULSE_RATE_CMOVAV | 141.7871345 - 151.7447355 | 75290 | 12882 | 17.11 | 123 | 121 |
| CODED2382 | DERIV1_MULTI_PH_CMOVAV | 5.026518E-7 - 1.763157E-6 | 25885 | 4478 | 17.30 | 125 | 121 |
| CODED2383 | DERIV1_CVP_CMOVSTD | 0.02994997 - 0.040792 | 34016 | 5860 | 17.23 | 124 | 121 |
| CODED2384 | MULTI_PCO2_CMOVSTD | 6.488084316 - 7.789054225 | 31857 | 5491 | 17.24 | 124 | 121 |
| CODED2385 | MULTI_ION_CMOVSTD | 0.714169555 - 1.814873399 | 25594 | 4412 | 17.24 | 124 | 121 |
| CODED2386 | DERIV2_MULTI_POT_CMOVAV | 9.227356E9 - 1.010527E-7 | 39964 | 6851 | 17.14 | 124 | 121 |
| CODED2387 | DERIV2_MULTI_BICARB_CMOVSTD | 1.692021E-9 - 6.077E-7 | 33410 | 5736 | 17.17 | 124 | 121 |
| CODED2388 | DERIV2_MULTI_BASE | 4.69537E10 - 1.913356E-9 | 33769 | 5793 | 17.15 | 124 | 121 |
| CODED2389 | NN_INTERVAL | 0.391617667 - 0.424661198 | 84693 | 14385 | 16.98 | 123 | 121 |
| CODED2390 | MULTI_PO2_VEN_CMOVAV | 44.16 - 45.475 | 23473 | 4039 | 17.21 | 124 | 121 |
| CODED2391 | DERIV2_CHLORIDE | -1.46469E-9 - -7.4057E-10 | 39332 | 6715 | 17.07 | 123 | 120 |
| CODED2392 | DERIV1_MULTI_ION | -4.59294E-6 - -7.7983E-7 | 32487 | 5558 | 17.11 | 123 | 120 |
| CODED2393 | DERIV2_RATIO | -0.00001545 - -6.32576E-6 | 76232 | 12928 | 16.96 | 122 | 120 |
| CODED2394 | MULTI_PO2 | 115 - 146 | 24239 | 4161 | 17.17 | 124 | 120 |
| CODED2395 | O2_SATURATON_CMOVSTD | 3.770735608 - 4.706207905 | 28442 | 4872 | 17.13 | 124 | 120 |
| CODED2396 | DERIV1_CREATININE | -7.76159E-7 - -3.64093E-7 | 39410 | 6718 | 17.05 | 123 | 120 |
| CODED2397 | HIBP_MEAN_CMOVAV | 69.00014798 - 74 | 72791 | 12334 | 16.94 | 122 | 120 |
| CODED2398 | DERIV2_MULTI_POT_CMOVSTD | 2.047386E-8 - 3.915641E-8 | 40006 | 6808 | 17.02 | 123 | 120 |
| CODED2399 | CALCIUM | 9.4 - 9.6 | 39741 | 6759 | 17.01 | 123 | 120 |
| CODED2400 | PHOSPHORUS_CMOVSTD | 0.98386991 - 1.063810176 | 38597 | 6566 | 17.01 | 123 | 120 |

| PATIENT | STARTDATE | P_DEAD1 | ID | CARDIAC | RENAL | RESPIRATORY | HEPATIE | HEMATOLOGY |
|---|---|---|---|---|---|---|---|---|
| uv_17a8d942 | 17JUL | 0.837234 | 0.0 | 40.0 | 0.0 | 18.0 | 0.0 | 0.0 |
| uv_17a8d942 | 18JUL | 0.818931 | 0.0 | 40.2 | 0.0 | 18.0 | 0.0 | 0.0 |
| uv_17a8d942 | 19JUL | 0.831449 | 0.0 | 37.5 | 0.0 | 18.0 | 0.0 | 0.0 |
| uv_17a8d942 | 20JUL | 0.660144 | 0.0 | 37.8 | 0.0 | 18.0 | 0.0 | 0.0 |
| uv_17a8d942 | 21JUL | 0.720858 | 0.0 | 38.9 | 0.0 | 18.0 | 0.0 | 0.0 |
| uv_17a8d942 | 22JUL | 0.645172 | 0.0 | 37.1 | 0.0 | 18.0 | 0.0 | 0.0 |
| uv_17a8d942 | 23JUL | 0.746791 | 0.0 | 36.4 | 0.0 | 18.0 | 0.0 | 0.0 |
| uv_17a8d942 | 24JUL | 0.869837 | 0.0 | 41.4 | 5.3 | 8.4 | 0.0 | 0.0 |
| uv_17a8d942 | 25JUL | 0.998454 | 7.6 | 43.7 | 67.2 | 30.4 | 0.0 | 32.4 |
| uv_17a8d942 | 26JUL | 0.999996 | 18.5 | 48.6 | 79.1 | 39.6 | 0.0 | 42.9 |
| uv_17a8d942 | 27JUL | 0.999999 | 17.2 | 49.2 | 82.2 | 37.6 | 8.1 | 42.4 |
| uv_17a8d942 | 28JUL | 1.000000 | 16.2 | 52.0 | 84.7 | 39.2 | 10.0 | 43.7 |
| uv_17a8d942 | 29JUL | 1.000000 | 16.0 | 51.4 | 84.2 | 40.6 | 10.0 | 44.8 |
| uv_17a8d942 | 30JUL | 1.000000 | 16.8 | 53.0 | 83.2 | 41.4 | 10.0 | 46.6 |
| uv_17a8d942 | 31JUL | 1.000000 | 16.2 | 51.3 | 86.8 | 39.7 | 10.0 | 44.1 |
| uv_17a8d942 | 01AUG | 1.000000 | 18.8 | 55.9 | 85.5 | 54.5 | 10.0 | 46.4 |
| uv_17a8d942 | 02AUG | 1.000000 | 17.7 | 56.4 | 85.1 | 70.3 | 10.0 | 46.5 |
| uv_17a8d942 | 03AUG | 1.000000 | 17.1 | 62.4 | 82.7 | 103.3 | 10.0 | 46.0 |
| uv_17a8d942 | 04AUG | 1.000000 | 17.6 | 60.9 | 85.3 | 105.7 | 10.0 | 46.6 |
| uv_17a8d942 | 05AUG | 0.999961 | 18.0 | 62.9 | 85.8 | 110.3 | 10.0 | 45.4 |
| uv_17a8d942 | 06AUG | 0.999848 | 17.2 | 66.4 | 85.1 | 105.0 | 10.0 | 46.6 |
| uv_17a8d942 | 07AUG | 0.999999 | 16.1 | 71.6 | 86.5 | 103.4 | 16.6 | 46.3 |
| uv_17a8d942 | 08AUG | 1.000000 | 17.0 | 68.8 | 86.0 | 103.9 | 35.9 | 45.2 |
| uv_17a8d942 | 09AUG | 1.000000 | 16.7 | 69.1 | 85.5 | 98.4 | 43.8 | 59.5 |
| uv_17a8d942 | 10AUG | 1.000000 | 17.8 | 70.3 | 83.9 | 99.7 | 44.9 | 65.7 |
| uv_17a8d942 | 11AUG | 1.000000 | 16.0 | 67.4 | 87.4 | 101.3 | 44.6 | 65.1 |
| uv_17a8d942 | 12AUG | 1.000000 | 18.0 | 64.7 | 84.7 | 105.4 | 36.1 | 65.5 |
| uv_17a8d942 | 13AUG | 1.000000 | 17.7 | 66.5 | 83.8 | 103.5 | 23.3 | 60.9 |
| uv_17a8d942 | 14AUG | 1.000000 | 17.4 | 65.8 | 83.4 | 101.1 | 12.9 | 44.7 |
| uv_17a8d942 | 15AUG | 1.000000 | 17.3 | 62.6 | 81.5 | 101.8 | 10.0 | 43.7 |
| uv_17a8d942 | 16AUG | 1.000000 | 17.0 | 650 | 81.1 | 103.3 | 10.0 | 42.5 |
| uv_17a8d942 | 17AUG | 1.000000 | 17.0 | 64.3 | 77.7 | 102.8 | 10.0 | 41.1 |
| uv_17a8d942 | 18AUG | 1.000000 | 17.3 | 60.0 | 77.6 | 86.9 | 4.5 | 36.7 |
| uv_17a8d942 | 19AUG | 0.925828 | 19.0 | 52.2 | 40.1 | 56.7 | 0.0 | 23.9 |

FIG. 14C

| Int | RANGE | PICU COUNT | DEAD COUNT | MORTALITY PERCENT | ALARM |
|---|---|---|---|---|---|
| 1 | 123.25 - 154.7372737 | 36,386 | 7,707 | 21.18 | FLAT |
| 2 | 124.7333323 - 135.7666037 | 36,438 | 10,775 | 29.55 | HIGH |
| 3 | 133.7777378 - 136.0452331 | 36,400 | 10,477 | 35.70 | HIGH |
| 4 | 130.0967742 - 136.04666657 | 36,389 | 6,384 | 17.47 | LOW |
| 5 | 138.6727253 - 137.0633333 | 28,592 | 977 | 2.90 | LOW |
| 6 | 137.0009058 - 137.6638462 | 36,360 | 1,795 | 24.96 | LOW |
| 7 | 1370004667 - 135 | 37,547 | 2,719 | 24.96 | LOW |
| 8 | 1390046667 - 100.3444478 | 30,404 | 2,877 | 7.99 | LOW |
| 9 | 140.30 - 144.0287190 | 75,950 | 7,470 | 30.42 | FLAT |
| 10 | 144083377 - 159 | 30,417 | 38,334 | 30.47 | HIGH |

| Int | RANGE | PICU COUNT | DEAD COUNT | MORTALITY PERCENT | ALARM |
|---|---|---|---|---|---|
| 1 | 0 1.000207398 | 36,150 | 11,500 | 12.18 | HIGH |
| 2 | 1,20000800 - 2300401077 | 36,204 | 210 | 0.27 | LOW |
| 3 | 331.3521322 - 2030370312 | 36,148 | 408 | 1.03 | LOW |
| 4 | 2344601122 - 3099707539 | 36,003 | 1,419 | 3.24 | LOW |
| 5 | 3.10166713 - 3.642343568 | 35,909 | 7,138 | 19.81 | FLAT |
| 6 | 3.545715605 - 4083188015 | 36, 3467 | 5,254 | 14.57 | LOW |
| 7 | 4.4859826100 - 4.490475027 | 36,007 | 13,006 | 30,26 | HIGH |
| 8 | 4.498720102 - 5.25237312 | 36,003 | 10,302 | 29.17 | HIGH |
| 9 | 4.498720103 - 5.938303117 | 36,383 | 14,575 | 40.00 | HIGH |
| 10 | 5.939778848 - 12.88670227 | 44,926 | 19,002 | 56.28 | HIGH |

LMPMML

```
<?xml version="1.0" encoding="utf-8" standalone="yes"?>
<PMML version="3.1"
  xmlns="http://www.dmg.org/PMML-3_1"
  xmlns:xsi="http://www.w3.org/2001/XMLSchema-instance">
  <Header copyright="copyright(c) 2002 SAS INSTITUTE Inc., Cary, NC, USA> All Rights Reserved.">
    <Application name="SAStr" version="9.1"/>
    <Timestamp>2009-07-09 10:28:15</Timestamp>
  </Header>
  <DataDictionary numberOfFields="2401">
    <DataField name="CODED1" displayName="UREA_NITROGEN_CMOVSTD: 16.39657339 - 27.47294123" optype="categorical" datatype="double"/>
    <DataField name="CODED10" displayName="DERIV1_ALT_CMOVSTD: 0.169115568 - 0.188912207" optype="categorical" datatype="double"/>
    <DataField name="CODED100" displayName="DERIVT_HR_ECG_2: -0.00017142 - 6.765583E-7" optype="categorical" datatype="double"/>
    <DataField name="CODED1000" displayName="DERIV2_MULTI_PCO2_CMOVSTD: 4.472721E-9 - 5.062997E-8" optype="categorical" datatype="double"/>
    <DataField name="CODED1001" displayName="DERIV2_INR_CMOVAV: -4.6668E-11 - -9.5463E-13" optype="categorical" datatype="double"/>
    <DataField name="CODED1002" displayName="DERIV1_CREATININE_CMOVAV: 3.042728E-7 - 9.530929E-7" optype="categorical" datatype="double"/>
    <DataField name="CODED1003" displayName="DERIV1_CO2: -0.00005617 - -0.00002828" optype="categorical" datatype="double"/>
    <DataField name="CODED1004" displayName="DERIV1_PROTEIN_TOTAL_CMOVSTD: 0.00001621 - 0.000229466" optype="categorical" datatype="double"/>
    <DataField name="CODED1005" displayName="DERIV1_MULTI_HEMA: -0.02649999 - 0.00011777" optype="categorical" datatype="double"/>
    <DataField name="CODED1006" displayName="PNN400: 0.992217899 - 0.99397504" optype="categorical" datatype="double"/>
    <DataField name="CODED1007" displayName="DERIV1_MULTI_BASE: -0.00012791 - -0.00005334" optype="categorical" datatype="double"/>
    <DataField name="CODED1008" displayName="DERIV1_ETCO2: 0.013668688 - 0.033916317" optype="categorical" datatype="double"/>
    <DataField name="CODED1009" displayName="MULTI_POT: 4.6 - 5" optype="categorical" datatype="double"/>
    <DataField name="CODED101" displayName="DERIV2_D_DIMER_QUANT: -8.2005BE-7 - -2.66792E-7" optype="categorical" datatype="double"/>
    <DataField name="CODED1010" displayName="DERIV2_ETCO2_CMOVAV: 0.000109508 - 0.256615646" optype="categorical" datatype="double"/>
    <DataField name="CODED1011" displayName="DERIV1_MULTI_POT_CMOVSTD: 0.000099646 - 0.000126988" optype="categorical" datatype="double"/>
    <DataField name="CODED1012" displayName="DERIV1_MULTI_ART_CMOVAV: -0.0005293 - 0.000954294" optype="categorical" datatype="double"/>
    <DataField name="CODED1013" displayName="DERIV2_ETCO2: -0.00158687 - -0.00063708" optype="categorical" datatype="double"/>
    <DataField name="CODED1014" displayName="DERIV2_MULTI_HEMA_CMOVSTD: 1.426777E-8 - 3.857822E-8" optype="categorical" datatype="double"/>
    <DataField name="CODED1015" displayName="DERIV2_ETCO2: 0.000563123 - 0.001238681" optype="categorical" datatype="double"/>
    <DataField name="CODED1016" displayName="DERIV2_MULTI_SODIUM: 7.32382E-10 - 6.369898E-9" optype="categorical" datatype="double"/>
    <DataField name="CODED1017" displayName="O2_SATURATION: 99.3 - 99.8" optype="categorical" datatype="double"/>
    <DataField name="CODED1018" displayName="DERIV1_ETCO2_CMOVSTD: 0.021234202 - 0.027710075" optype="categorical" datatype="double"/>
    <DataField name="CODED1019" displayName="DERIV1_MAGNESIUM_CMOVSTD: 0.000024436 - 0.000036305" optype="categorical" datatype="double"/>
    <DataField name="CODED102" displayName="DERIV2_HR_ECG-2: -0.00001333 - 2.660875E-6" optype="categorical" datatype="double"/>
    <DataField name="CODED1020" displayName="DERIV2_MULTI_ART: -0.00077248 - -0.00019346" optype="categorical" datatype="double"/>
    <DataField name="CODED1021" displayName="DERIV2_MULTI_ION: 5.40931E-9 - 0.038393959" optype="categorical" datatype="double"/>
    <DataField name="CODED1022" displayName="MULTI_HEMA_CMOVSTD: 2.621340987 - 3.074556879" optype="categorical" datatype="double"/>
    <DataField name="CODED1023" displayName="DERIV2_ABSOLUTE_NEUT_CT: -2.31162E-6 - -6.7396E-10" optype="categorical" datatype="double"/>
    <DataField name="CODED1024" displayName="MULTI_BASE_CMOVSTD: 4.571765489 - 5.274077818" optype="categorical" datatype="double"/>
    <DataField name="CODED1025" displayName="DERIVT_ETCO2_CMOVSTD: 0.027710256 - 0.034521434" optype="categorical" datatype="double"/>
    <DataField name="CODED1026" displayName="INR_CMOVAV: 0.95 - 1.1875" optype="categorical" datatype="double"/>
    <DataField name="CODED1027" displayName="DERIV1_PLATELET_COUNT: 0.000243019 - 0.000487572" optype="categorical" datatype="double"/>
    <DataField name="CODED1028" displayName="DERIV2_MULTI_PCO2_CMOVAV: -0.00002564 - 0.00001775" optype="categorical" datatype="double"/>
    <DataField name="CODED1029" displayName="DERIV1_MULTI_PO2_CMOVAV: -3.51260854 - -0.00244864" optype="categorical" datatype="double"/>
    <DataField name="CODED103" displayName="FIBRINOGEN_F_T_CMOVSTD: 63.00905511 - 69.99965986" optype="categorical" datatype="double"/>
    <DataField name="CODED1030" displayName="UREA_NITROGEN_CMOVSTD: 3.342769617 - 3.983264586" optype="categorical" datatype="double"/>
    <DataField name="CODED1031" displayName="DERIV2_CALCIUM: -3.17811E-8 - -2.2886E-10" optype="categorical" datatype="double"/>
    <DataField name="CODED1032" displayName="DERIV1_HEART_RATE: -0.00018537 - 0.000171563" optype="categorical" datatype="double"/>
    <DataField name="CODED1033" displayName="MULTI_ION_CMOVSTD: 0.418296519 - 0.489322257" optype="categorical" datatype="double"/>
    <DataField name="CODED1034" displayName="MULTI_HEMO: 12.8 - 13.7" optype="categorical" datatype="double"/>
    <DataField name="CODED1035" displayName="DERIVT_PLATELET_COUNT_CMOVSTD: 0.002272894 - 0.005793821" optype="categorical" datatype="double"/>
    <DataField name="CODED1036" displayName="MAGNESIUM: 2.2 - 2.3" optype="categorical" datatype="double"/>
    <DataField name="CODED1037" displayName="MULTI_SODIUM_CMOVAV: 135.8571429 - 136.2666667" optype="categorical" datatype="double"/>
    <DataField name="CODED1038" displayName="DERIV2_CO2_CMOVAV: 3.36591E-10 - 9.83044E-10" optype="categorical" datatype="double"/>
    <DataField name="CODED1039" displayName="DERIV2_ETCO2_CMOVSTD: 0.000926837 - 0.00122" optype="categorical" datatype="double"/>
    <DataField name="CODED104" displayName="DERIV2_URIC_ACID: 2.97076E-13 - 3.06137E-12" optype="categorical" datatype="double"/>
    <DataField name="CODED1040" displayName="MULTI_ART_CMOVSTD: 1.662423176 - 2.336502839" optype="categorical" datatype="double"/>
    <DataField name="CODED1041" displayName="DERIVT_TEMPERATURE: -0.00129574 - -0.00009641" optype="categorical" datatype="double"/>
    <DataField name="CODED1042" displayName="DERIV2_PROTEIN_TOTAL: -2.2461E-12 - -1.5411E-12" optype="categorical" datatype="double"/>
    <DataField name="CODED1043" displayName="DERIV2_PROTEIN_TOTAL_CMOVAV: 1.41463E-10 - 4.38957E-10" optype="categorical" datatype="double"/>
    <DataField name="CODED1044" displayName="DERIV1_MULTI_PH_CMOVSTD: 0.000049497 - 0.000241969" optype="categorical" datatype="double"/>
    <DataField name="CODED1045" displayName="DERIV2_MULTI_LACTATE_CMOVSTD: 2.923545E-6 -0.000072368" optype="categorical" datatype="double"/>
    <DataField name="CODED1046" displayName="HEART_RATE_CMOVAV: 153.4790323 - 268.9025424" optype="categorical" datatype="double"/>
    <DataField name="CODED1047" displayName="DERIVT_TEMPERATURE_CMOVAV: 2.10533E-17 - 0.000028906" optype="categorical" datatype="double"/>
    <DataField name="CODED1048" displayName="TEMPERATURE_CMOVAV: 37.55041667 - 37.89931773" optype="categorical" datatype="double"/>
    <DataField name="CODED1049" displayName="PHOSPHORUS: 6.8 - 9.2" optype="categorical" datatype="double"/>
    <DataField name="CODED105" displayName="URIC_ACID_CMOVSTD: 0.892728562 - 1.459514247" optype="categorical" datatype="double"/>
    <DataField name="CODED1050" displayName="DERIV1_MULTI_PH: 2.653449E-6 - 0.000011868" optype="categorical" datatype="double"/>
    <DataField name="CODED1051" displayName="DERIV1_MULTI_POT: -0.00007468 - 0.00003677" optype="categorical" datatype="double"/>
    <DataField name="CODED1052" displayName="TEMPERATURE_CMOVSTD: -0.00010851 - 0.021978418" optype="categorical" datatype="double"/>
```

FIG. 18A

LMPMML

```xml
<?xml version="1.0" encoding="utf-8" standalone="yes"?>
<PMML version="3.1"
 <xmlns="http://www.dmg.org/PMML-3_1"
 <xmlns:xsi="http://www.w3.org/2001/XMLSchema-instance">
  <Header copyright="copyright(c) 2002 SAS INSTITUTE Inc., Cary, NC, USA> All Rights Reserved.">
   <Application name="SAS(r)" version="9.1"/>
   <Timestamp>2009-07-09 09:56:09</Timestamp>
  </Header>
  <DataDictionary numberOfFields="1033">
   <DataField name="CODED1" displayName="DERIV2_MULTI_ION_CMOVAV: 1.734399E-8 - 1.776157E-8" optype="categorical" datatype="double"/>
   <DataField name="CODED10" displayName="DERIV1_MULTI_LACTATE_CMOVAV: -5.56887E-6" optype="categorical" datatype="double"/>
   <DataField name="CODED100" displayName="MULTI_LACTATE_CMOVSTD: 0.47934547 - 0.480319187" optype="categorical" datatype="double"/>
   <DataField name="CODED1000" displayName="DERIV1_NN_INTERVAL_CMOVSTD: 0.236848969 - 0.368501314" optype="categorical" datatype="double"/>
   <DataField name="CODED1001" displayName="DERIV1_MULTI_LACTATE_CMOVAV: 0.000010215 - 0.000099244" optype="categorical" datatype="double"/>
   <DataField name="CODED1002" displayName="MULTI_PO2_VEN: 32 -33" optype="categorical" datatype="double"/>
   <DataField name="CODED1003" displayName="DERIV2_HEART_RATE_CMOVSTD: 0.006816331 - 0.008036703" optype="categorical" datatype="double"/>
   <DataField name="CODED1004" displayName="HEART_RATE_CMOVSTD: 3.579963781 - 4.807204951" optype="categorical" datatype="double"/>
   <DataField name="CODED1005" displayName="DERIV1_SPO2_PULSE_RATE: -0.12506479 - -0.05671283" optype="categorical" datatype="double"/>
   <DataField name="CODED1006" displayName="DERIV2_SPO2_PULSE_RATE: 0.004817804 - 0.011495646" optype="categorical" datatype="double"/>
   <DataField name="CODED1007" displayName="DERIV2_HR_ECG_2: -0.00879819 - -0.00444886" optype="categorical" datatype="double"/>
   <DataField name="CODED1008" displayName="RATIO: 0.377831205 - 0.456531693" optype="categorical" datatype="double"/>
   <DataField name="CODED1009" displayName="NIBP_MEAN: 72.00103684 - 77" optype="categorical" datatype="double"/>
   <DataField name="CODED101" displayName="MULTI_PCO2_VEN_CMOVAV: 71.2173913 - 72.31818182" optype="categorical" datatype="double"/>
   <DataField name="CODED1010" displayName="DERIV1_MULTI_ION_CMOVSTD: 0.000407608 - 0.000700346" optype="categorical" datatype="double"/>
   <DataField name="CODED1011" displayName="DERIV1_RESP_RATE_CMOVSTD: 0.01622572 - 0.019825899" optype="categorical" datatype="double"/>
   <DataField name="CODED1012" displayName="SPO2: 89.62988647 - 93.8" optype="categorical" datatype="double"/>
   <DataField name="CODED1013" displayName="DERIV1_SPO2: 0.002097087 - 0.015117552" optype="categorical" datatype="double"/>
   <DataField name="CODED1014" displayName="DERIV1_RESP-RATE: -0.08696604 - -0.02060965" optype="categorical" datatype="double"/>
   <DataField name="CODED1015" displayName="DERIV1_RESP_RATE_CMOVAV: -0.00340129 - 0.001206744" optype="categorical" datatype="double"/>
   <DataField name="CODED1016" displayName="NN_INTERVAL: 0.687847487 - 1.386134038" optype="categorical" datatype="double"/>
   <DataField name="CODED1017" displayName="DERIV2_NN_INTERVAL_CMOVAV: 0.014283031 - 0.046900061" optype="categorical" datatype="double"/>
   <DataField name="CODED1018" displayName="SPO2: 98.91534705 - 99.84375" optype="categorical" datatype="double"/>
   <DataField name="CODED1019" displayName="DERIV2_SPO2: 0.00061204 - 0.001579882" optype="categorical" datatype="double"/>
   <DataField name="CODED102" displayName="DERIV1_MULTI_BICARB_CMOVAV: 0.00008175 - 0.000082146" optype="categorical" datatype="double"/>
   <DataField name="CODED1020" displayName="DERIV1_MULTI_ION: -0.00109469 - -0.00002736" optype="categorical" datatype="double"/>
   <DataField name="CODED1021" displayName="DERIV1_RATIO_CMOVAV: -0.00001006 - 3.4143E-5" optype="categorical" datatype="double"/>
   <DataField name="CODED1022" displayName="NN600: 1 -3" optype="categorical" datatype="double"/>
   <DataField name="CODED1023" displayName="DERIV2_HR_ECG_2: -1.00686608 - -0.00879864" optype="categorical" datatype="double"/>
   <DataField name="CODED1024" displayName="NN_INTERVAL: 0.441642062 - 0.471441857" optype="categorical" datatype="double"/>
   <DataField name="CODED1025" displayName="DERIV2_MULTI_ION_CMOVSTD: 1.364081E-7 - 2.547968E-7" optype="categorical" datatype="double"/>
   <DataField name="CODED1026" displayName="DERIV2_SPO2_CMOVAV: 0.00077328 - 0.000186636" optype="categorical" datatype="double"/>
   <DataField name="CODED1027" displayName="DERIV2_PLATELET_COUNT: -2.94728E-9 - -1.5087E-9" optype="categorical" datatype="double"/>
   <DataField name="CODED1028" displayName="PNN400: 0.02293578 - 0.142857143" optype="categorical" datatype="double"/>
   <DataField name="CODED1029" displayName="DERIV2_HEART_RATE_CMOVAV: -0.00016189 - -0.00004036" optype="categorical" datatype="double"/>
   <DataField name="CODED103" displayName="MULTI_BASE_CMOVSTD: 6.397148302 - 6.444158442" optype="categorical" datatype="double"/>
   <DataField name="CODED1030" displayName="DERIV1_SPO2: 0.015118904 - 0.037379534" optype="categorical" datatype="double"/>
   <DataField name="CODED1031" displayName="NUM_SECS: 118 - 129" optype="categorical" datatype="double"/>
   <DataField name="CODED1032" displayName="PNN500: 0.3233709163 - 0.610859729" optype="categorical" datatype="double"/>
   <DataField name="CODED104" displayName="DERIV2_UREA_NITROGEN_CMOVAV: -2.6195E-10 - -1.2848E-10" optype="categorical" datatype="double"/>
   <DataField name="CODED105" displayName="MULTI_LACTATE: 1.5 - 1.8" optype="categorical" datatype="double"/>
   <DataField name="CODED106" displayName="DERIV2_MULTI_BASE_CMOVAV: 5.727657E-08 - 6.723668E-8" optype="categorical" datatype="double"/>
   <DataField name="CODED107" displayName="DERIV2_MULTI-PH_VEN: -1.1534E-10 - -2.980E-11" optype="categorical" datatype="double"/>
   <DataField name="CODED108" displayName="MULTI_ION_CMOVAV: 4.093846154 - 4.45624" optype="categorical" datatype="double"/>
   <DataField name="CODED109" displayName="MULTI_ION: 4.69 - 4.77" optype="categorical" datatype="double"/>
   <DataField name="CODED11" displayName="DERIV1_MULTI_PH_CMOVAV: -9.68462E-7" optype="categorical" datatype="double"/>
   <DataField name="CODED110" displayName="DERIV1_MULTI_PH_VEN_CMOVSTD: 2.009864E-6 - 2.622579E-6" optype="categorical" datatype="double"/>
   <DataField name="CODED111" displayName="DERIV1_MAGNESIUM_CMOVAV: 6.650743E-7 - 1.76845E-6" optype="categorical" datatype="double"/>
   <DataField name="CODED112" displayName="DERIV2_MULTI_LACTATE_CMOVAV: 1.33866E-10 - 6.68725E-10" optype="categorical" datatype="double"/>
   <DataField name="CODED113" displayName="DERIV1_MULTI_LACTATE: -9.73923E-6 - -2.46708E-6" optype="categorical" datatype="double"/>
   <DataField name="CODED114" displayName="MULTI_PO2_VEN_CMOVSTD: 4.855041562 - 8.401710813" optype="categorical" datatype="double"/>
   <DataField name="CODED115" displayName="DERIV2_MAGNESIUM: 7.53241E-10 - 1.910706E-9" optype="categorical" datatype="double"/>
```

*FIG. 18B*

METHODS, SYSTEMS, AND COMPUTER READABLE MEDIA FOR EVALUATING A HOSPITAL PATIENT'S RISK OF MORTALITY

PRIORITY CLAIM

This application is a continuation of PCT International Patent Application No. PCT/US2011/042416 filed Jun. 29, 2011, which claims the benefit of U.S. Provisional Patent Application Ser. No. 61/359,708, filed Jun. 29, 2010; this application is also a continuation-in-part of U.S. patent application Ser. No. 12/302,008, filed Nov. 13, 2009, which is a 371 of PCT International Patent Application No. PCT/US2007/012736, filed May 30, 2007, which claims the benefit of U.S. Provisional Patent Application Ser. No. 60/809,283, filed May 30, 2006, the disclosures of which are incorporated herein by reference in their entireties.

GOVERNMENT INTEREST

This invention was made with Government support under Grant No. HD049935 awarded by National Institutes of Health. The government has certain rights in the invention.

TECHNICAL FIELD

The subject matter described herein relates to analyzing data regarding hospital patients. More particularly, the subject matter described herein relates to methods, systems, and computer readable media for evaluating a hospital patient's risk of mortality.

BACKGROUND

By the year 2010 there will be approximately 5,500 pediatric intensive care unit (PICU) beds, about 22,000 neonatal intensive care unit (NICU) beds, and about 110,000 non-intensive care (non-ICU) pediatric care beds in the United States of America. Rendering care to these hospitalized children represents a large, significant, and growing cost to health care expense. The importance of intensive care and non-intensive care monitoring in patient safety is recognized as a priority by the Joint Commission on Accreditation of Hospital Organizations. Intensive care and non-intensive care monitors are used to continuously evaluate the clinical status of patients and track their response to a wide range of interventions. Despite tremendous advancements in computer technology and bioinformatics, intensive care and non-intensive care monitoring devices have not provided significantly new information to bedside caregivers. Simplified cardiopulmonary monitoring is now routinely performed in hospitalized non-intensive care patients.

Rapid Response (RR) teams have been established to rescue non-ICU pediatric patients who are decompensating and in need of critical care evaluation. These teams are triggered by any health care provider (nurse, respiratory therapist, physician, etc.) or family members resulting in a stat evaluation by an expert team of health care providers that can initiate lifesaving support and transfer patients to an ICU. These teams have been shown to be effective at saving the lives of both pediatric and adult hospitalized inpatients.

Software tools are available for evaluating a patient's risk of mortality for patients in PICU, NICU and non-ICU pediatric facilities. However, conventional tools only evaluate a patient's risk of mortality based on raw variables considered individually. Models that evaluate a patient's risk of mortality based on raw variables considered individually lack accuracy and lead to false alarms. For example, conventional monitors that monitor intensive care patients' vital signs alarm frequently due to variability in the raw data, even when patients are not at risk of imminent death. As a result, hospital staff and physicians often ignore such alarms.

Accordingly, there exists a long felt need for methods, systems, and computer readable media for evaluating a hospital patient's risk of mortality.

SUMMARY

The subject matter includes methods, systems, and computer readable media for evaluating a hospital patient's risk of mortality. According to one aspect of the subject matter described herein, a method for evaluating a hospital patient's risk of mortality is provided. The method includes collecting data from physiologic signals generated by patient monitors, physiologic signals of organ function, and demographic information for a patient. The method further includes determining a measure of the variability of at least one of the physiologic signals. The method further includes analyzing data and the measure of variability to determine whether a value for a particular physiologic or demographic variable falls within a critical interval for the variable that indicates that the value is predictive of mortality or survival. Each time a value for a physiological or demographic variable for the patient falls within a critical interval, the method includes recording the occurrence of an event for the patient. The method further includes counting the number of events for the patient over a time period. The method further includes, generating, based on the count output perceptible by a human user that indicates the patient's risk of mortality or likelihood of survival.

The subject matter described herein can be implemented in software in combination with hardware and/or firmware. For example, the subject matter described herein can be implemented in software executed by a processor. In one exemplary implementation, the subject matter described herein can be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

Preferred embodiments of the subject matter described herein will now be explained with reference to the accompanying drawings, wherein like reference numerals represent like parts, of which:

FIGS. 5A and 5B are tables respectively illustrating statistical measures for variables for live and dead PICU patients that may be used by the system illustrated in FIG. 2 to evaluate a given patient's risk of mortality according to an embodiment of the subject matter described herein;

FIGS. 6A and 6B are tables illustrating statistical measures for additional variables for dead PICU and live PICU patients that may be used by the system illustrated in FIG. 2 to evaluate a given patient's risk of mortality according to an embodiment of the subject matter described herein;

FIG. 7 is a table illustrating the dividing of data points into critical intervals for a PICU patient according to an embodiment of the subject matter described herein;

FIGS. 8A and 8B are tables illustrating exemplary statistical measures for different variables for dead PICU and live PICU patients according to an embodiment of the subject matter described herein;

FIGS. 9A and 9B are tables illustrating exemplary measures of patient physiological data that may be obtained and used by the system illustrated in FIG. 2 to evaluate a given patient's risk of mortality according to an embodiment of the subject matter described herein;

FIGS. 10A and 10B illustrate variables, intervals, and statistical measures that may be used by the system illustrated in FIG. 2 to evaluate a hospital patient's risk of mortality according to an embodiment of the subject matter described herein;

FIGS. 11A and 11B illustrate intervals that may be used by the system in FIG. 2 to evaluate a patient's risk of mortality according to an embodiment of the subject matter described herein;

FIGS. 14A-14C are tables illustrating counts of multi-feed transformations on expanded PICU data where derivatives and second derivatives are computed to determine measures of variability of the variable being analyzed;

FIG. 18A is a partial predictive model markup language (PMML) listing of a model for evaluating risk of mortality for a PICU patient according to an embodiment of the subject matter described herein;

FIG. 18B is a partial PMML listing of a model for evaluating risk of mortality for a rapid response (RR) patient according to an embodiment of the subject matter described herein;

DETAILED DESCRIPTION

Figure 1:
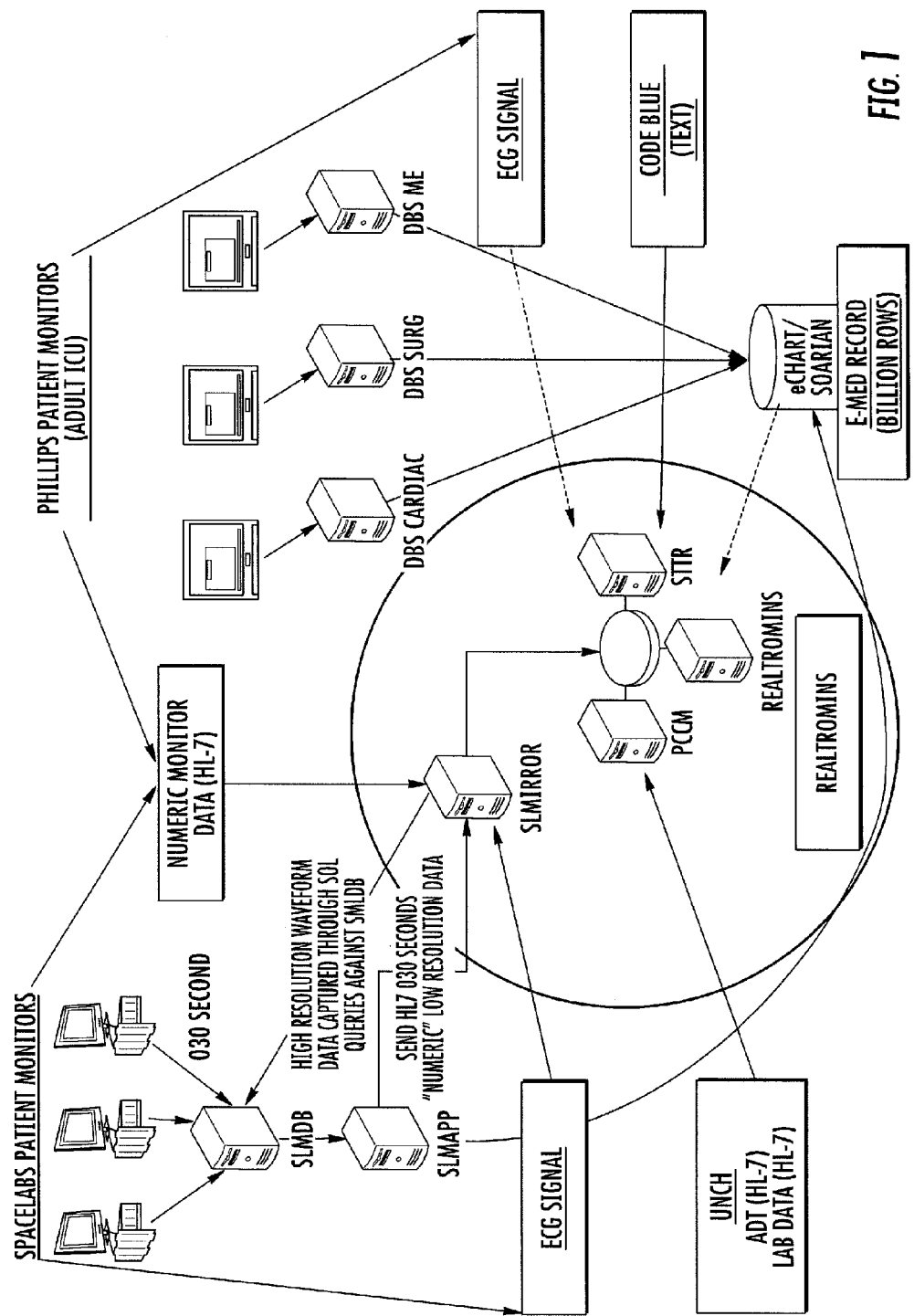
FIG. 1 is a block diagram illustrating exemplary overall components of an embodiment of the subject matter described herein.

In accordance with the subject matter disclosed herein, systems, methods, and computer readable media are provided for evaluating a hospital patient's risk of mortality. One exemplary implementation of the subject matter described herein is referred to as REALTROMINS, which is an acronym for REAL Time Risk of Mortality and INStability. REALTROMINS is a medical device for critically ill patients that integrates and analyzes numerous inputs: 1) real time continuous physiologic signals (e.g. electrocardiogram); 2) advanced measures of variability of these signals (e.g. spectral analysis); 3) physiologic based measures of organ function (e.g. serum glucose) and their variability; and 4) demographic and diagnosis related predictors of mortality; creating a real time, continuously updated risk of mortality score to aid clinicians in administering medical care. Described herein are REALTROMINS devices and methods for use in patient populations comprising premature infants in a neonatal intensive care unit (NICU; Neonatal REALTROMINS) and hospitalized children outside the ICU but in a non-ICU pediatric care facility and/or under the care and supervision of a Rapid Response (RR) team (Rapid Response REALTROMINS). Also described herein are REALTROMINS devices and methods for use in the PICU. The REALTROMINS devices and methods can guide medical decision making resulting in earlier initiation or withdrawal of costly and risky therapeutic interventions to improve patient outcomes. In addition, the presently disclosed subject matter can decrease healthcare costs by better matching expensive and limited: 1) human resources (physician, nursing, etc.) and 2) hospital facilities (intensive care beds) to the changing needs of critically ill and hospitalized patients.

REALTROMINS is a bioinformatics technology designed to continuously assess the changing risk of mortality of critically ill pediatric patients and track the success or failure of ongoing medical interventions. Described herein are REALTROMINS technologies to be utilized in treating patients in PICU, NICU and non-ICU pediatric settings. Bedside caregivers can determine which therapies are leading to a decrease in risk while an increased mortality risk would trigger new approaches to the clinical problem. Patient outcomes can improve by displaying the overall risk score and the individual components contributing to that risk. By way of example and not limitation, heart rate variability has been shown to be highly predictive of mortality in a wide variety of critical illnesses in both adults and children. While not intended to be bound by any single theory or mechanism of action, the concept is that healthy biological systems are in a natural state of chaos and when critical illness develops, this natural variability is lost. Analysis of the low frequency (LF) and high frequency (HF) spectral content of heart rate variability, with calculation of a ratio of these two areas, has been predictive of mortality. As such, in some embodiments REALTROMINS couples these metrics, along with others, into an advanced multivariate analysis using SAS Enterprise Miner Software (SAS Institute, Cary, N.C., United States of America). In other embodiments, these metrics are assigned to critical intervals and used to generate hospital patient scores without using SAS Enterprise Miner Software.

Research Design and Methods

Projects and experiments were designed for the generation and collection of data for the development of the Neonatal REALTROMINS and Rapid Response REALTROMINS. A prospective cohort study was used for the estimation and validation data sets. A sixteen-bed PICU (REALTROMINS), 45-bed NICU (Neonatal REALTROMINS), and a 69 non-ICU bed (Rapid Response REALTROMINS) tertiary care university based children's hospital was used in the studies. Annual admissions to the PICU, NICU, and non-ICU beds were approximately 1,000, 750, and 3,100, respectively. Patients ranged in age from 0 (as young as 22 weeks gestation) to 18 years, encompassing the full range of pediatric medical and surgical diagnoses. In the PICU, the male to female ratio is 1.27:1, and a diverse racial background is represented. The racial and ethnic breakdowns are as follows: 48% white, 31% black and 21% Hispanic and other races. Patient Enrollment Criteria: For the estimation (50% of patients) and validation (50% of patients) data sets, all patients admitted to the PICU, NICU, and non-ICU beds were enrolled over 9 months, and a comparison between survivors and non-survivors was examined. Since few patients died in the non-ICU beds additional outcome measures, such as transfer to the PICU, triggering a code blue (cardiopulmonary arrest) or Rapid Response team dispatch were examined.

Summary of Data Sources and Information Flow

As depicted in FIG. 1, the following continuous physiologic signals were obtained in all subjects as determined by the clinical needs of the patient: 1) cardiac a) electrocardiogram, b) invasive arterial blood pressure, c) invasive central venous pressure; 2) respiratory a) respiratory plethysmograph, b) pulse oximetry, c) end tidal carbon dioxide concentrations; and 3) continuous temperature. These continuous digital data streams were written to a central server in an SQL database structure every 8 seconds. This database contained information detailing which monitor (i.e. patient) data is streaming from, UTC time stamps, and the individual data elements. All data were stored and backed up using standard procedures (RAID 5 hard drive configuration and digital tape).

The electrocardiogram (ECG) was digitized and a java based algorithm was used to detect the fiducial point (R wave of the ECG) from which the RR interval (time between R peaks), heart period, and heart rate (HR) time series were derived. The front end loader manages data capture. This component consists of the open source Mirth HL-7 engine for capture of all HL-7 data feeds and a custom Java application that captures real-time ICU monitor data every 30 seconds (configurable) from the vendor's transactional database via a JDBC database connection. At the point of capture, the UTC time stamp, patient location, and patient IDs are standardized and data is then forwarded to the messaging system. A Java-based real-time patient system (RTPS) captures all data packets from the messaging system for pre-selected patient locations. The RTPS dynamically links all data packets for each patient and stores the data in-memory in a custom multivariate time series representation. The custom representation allows each variable to be stored at the variable's temporal resolution in addition to providing access to packets that provide all variable values during a fixed time window (typically 2 minutes). Signal processing and preprocessing algorithms are applied to the time series, which results in the creation of new time series variables. Decision support algorithms can then be applied on a continuous basis to the incoming time series data. Since a patient can be monitored for days to months at a time, the in-memory data is limited to the maximum time needed for signal processing and decision support while older data is pushed to a transactional database within the RTPS. A second Java application monitors the RTPS to detect patients that have been discharged from a location. Once detected, all data on that patient is extracted from the RTPS and moved to the data archival system. As part of this process, the patient data is converted from the custom time series representation to a format amendable to model development.

Spectral analyses were then performed. The HR time series was interpolated to achieve a uniform sampling interval and normalized to mean zero variation from the mean. The amplitude spectrum was generated using the Fast Fourier transform (FFT). The power spectrum was derived from the amplitude spectra and used to determine frequency band specific (ultra-low, very low, low, and high frequency) variance of the HR time series for statistical tests of significance. Sequential records of Power spectra were generated once every 128 beats (approximately every 1-2 minutes in children). These results were then entered into the statistical and neural network software.

Physiologic based indices of organ function were obtained at an hourly frequency (i.e. urine output) or intermittently (i.e. serum glucose) according to patient care needs. Physiologic based measures of organ function included: 1) cardiac indicia, comprising non-invasive blood pressure (hourly systolic and diastolic), lactate level; 2) respiratory indicia, comprising respiratory rate, pH, $PCO_2$, $PO_2$, $HCO_3$, $O_2$ saturation, fractional inspired oxygen concentration (hourly); 3) neurologic indicia, comprising Glasgow coma score (hourly), pupillary reactions (hourly); 4) fluid indicia, comprising sodium, potassium, glucose, urea nitrogen, creatinine concentrations, ionized calcium, whole blood glucose measurements, urine output (hourly), hourly fluids administered (IV and/or enteral), weight on admission; 5) hematologic indicia, comprising hemoglobin, platelet count, prothrombin time-INR, partial thromboplastin time, D-dimers; 6) hepatic indicia, comprising bilirubin, transaminase, albumin, total protein; and 7) immunologic indicia, comprising temperature (hourly if not continuous), white cell count (total), absolute neutrophil count, absolute lymphocyte count, c reactive protein. Changes in these variables over time were investigated using the SAS procedure EXPAND to calculate first and second derivatives.

Demographic and diagnosis related predictors: 1) age; 2) general diagnostic groups (e.g., oncologic disease); 3) pre ICU risk factors (e.g., cardiopulmonary resuscitation); and 4) other (e.g., cardiac pacing) were recorded. For NICU patients, gestational age, birth weight, APGAR score at 1 and 5 minutes, and high risk maternal risk factors (chorioamnionitis, placental abruption, etc.) were recorded.

Model Building

Quantitative Target Modeling System (QTMS V3—Applied Multivariate Algorithms, Manorville, N.Y.) are proprietary SAS macros used for transforming raw information into optimized "bins" or intervals to be used with SAS EM5.2 neural network model building suite. Raw physiologic information was transformed creating composite variables scanned and summarized by QTMS. This calculated a variety of statistics for each interval found within each variable including lift from base, t-tests, chi-square analysis, indices, missing data, and confidence intervals. Significant intervals from each variable were selected depending on a specified lift from base criteria. Calculating all available model building techniques, the RULE INDUCTION approach delivered the best set of specificity and sensitivity rates within the model comparison wizard. Neonatal REALTROMINS and Rapid Response REALTROMINS were created by streaming and analyzing data from the NICU and non ICU beds, respectively, into a REALTROMINS algorithm.

Results

Twenty-eight pediatric patients matched on age, sex, and diagnosis, half of whom died, were used for the analytic set for the neural network building process. PICU Admission Data: The first four hours of data from the 28 matched patients were partitioned out for analyses and outcome (DIED vs. SURVIVE) recorded. This resulted in an analytic data set of 3360 records (1680 SURVIVE packets and 1680 DIED packets). Each patient thus produced 120 records for the first four hours at two minute intervals. The training data set utilized 80% of the data packets with a random 20% hold out sample of packets used to validate. The predictive capabilities of the model are demonstrated below. Identical results were found in the validation data set.

| Actual Patient Outcome | | | |
| --- | --- | --- | --- |
| | Survivor | Died | Total |
| Predicted to Survive | 1329 | 21 | 1350 |
| Predicted to Die | 15 | 1322 | 1337 |
| Total | 1344 | 1343 | 2687 |
| Predictive Capability | | | |
| Sensitivity | 98.44% | | |
| Specificity | 98.88% | | |
| False Positive | 1.12% | | |
| False Negative | 1.56% | | |

The PICU Length of Stay (LOS): This set was analyzed representing 57,000 REALTROMINS scores with LOS from 0.29 to 12.73 days with a cumulative length of stay of 79.41 days. The predictive capabilities of the model are demonstrated below. Six of fourteen survivors and 4/14 patient deaths had 100% correct classification during the PICU LOS.

| Actual Patient Outcome | | | |
| --- | --- | --- | --- |
| | Survivor | Died | Total |
| Predicted to Survive | 17,248 | 5,636 | 22,884 |
| Predicted to Die | 6,936 | 27,354 | 34,290 |
| Total | 24,184 | 32,990 | 57,174 |
| Predictive Capability | | | |
| Sensitivity | 82.92% | | |
| Specificity | 71.32% | | |
| False Positive | 20.23% | | |
| False Negative | 24.63% | | |

Survivor Validation Dataset: An additional sixteen survivors were then analyzed during their PICU LOS representing about 25,000 REALTROMINS Scores with LOS from 0.23 to 6.36 days with 35.4 cumulative patient days. The predictive capabilities of the model were nearly identical to the PICU LOS data above.

Figure 2:
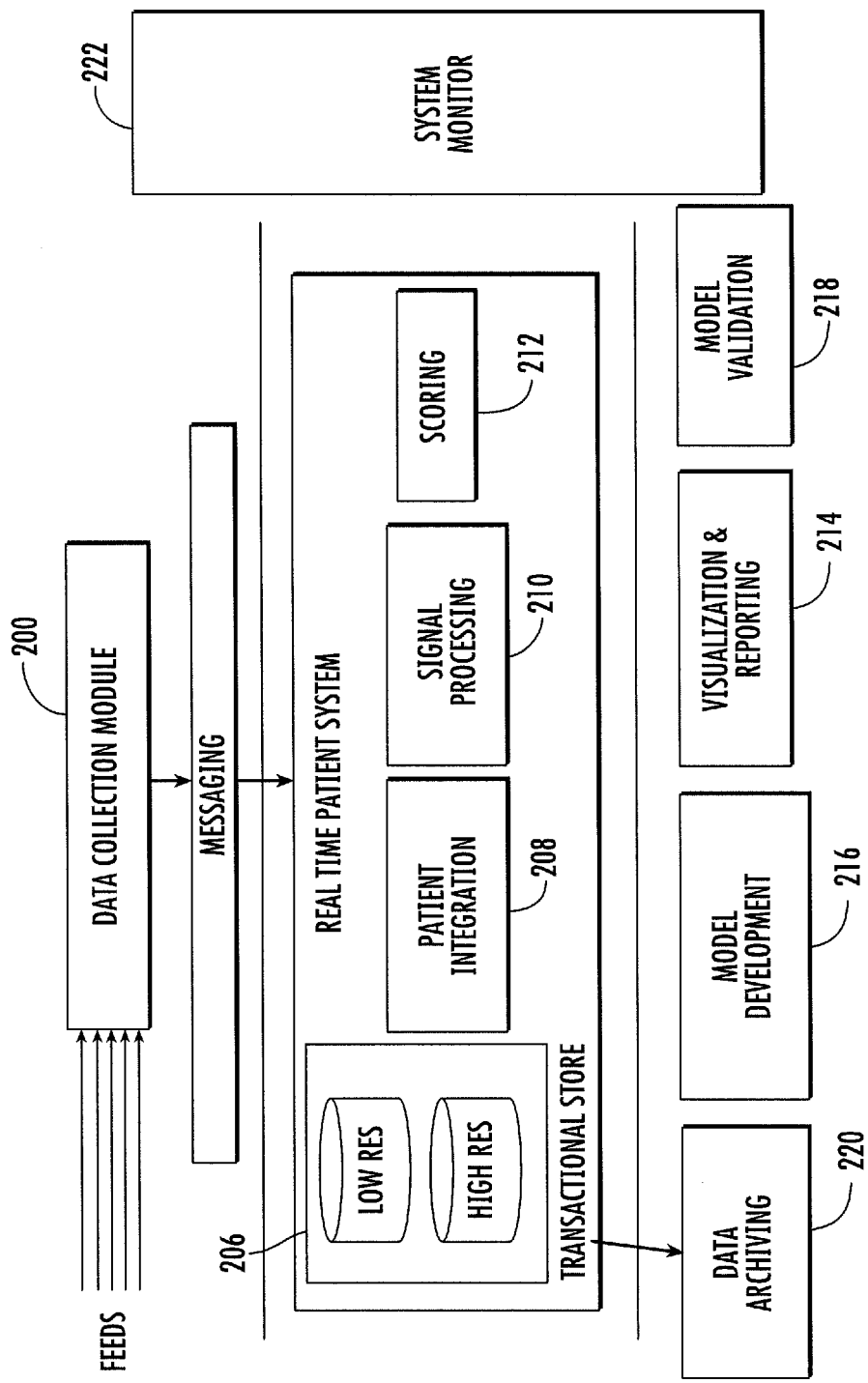
FIG. 2 is a block diagram illustrating exemplary components of a system for evaluating a hospital patient's risk of mortality according to an embodiment of the subject matter described herein.

FIG. 2 is a block diagram illustrating an exemplary system for evaluating a hospital patient's risk of mortality according to an embodiment of the subject matter described herein. Referring to FIG. 2, the system includes a data collection module 200 that receives inputs, referred to a feeds in FIG. 2. These inputs may be physiologic signals generated by patient monitors, physiologic signals of organ function, and demographic information for a patient. Data collection module 200 may separate the data into time stamped packets. For example, where the data comprises signals output from an electrocardiogram, each data packet may include a time stamp and a peak, representing a peak ECG voltage. Messaging module 202 communicates the data packets to a real-time patient monitoring system 204. Real-time patient monitoring system 204 includes transactional store 206, where high and low resolution data packets are stored; patient integration module 208, which segregates the data packets into groups for individual patients; and a signal processing module 210, which generates measures of variability of at least some of the physiologic signals. As will be described in more detail below, signal processing module 210 may receive ECG signals and use a covariance function to remove corruption from the ECG signals.

Real-time patient monitoring system 204 may also include a scoring module 212 which generates a score that indicates a patient's risk of mortality or likelihood of survival. In one exemplary implementation, scoring module 212 may determine whether a particular physiologic or demographic variable for a patient falls within a critical interval for variable that indicates that the value is predictive of mortality or likelihood of survival. Examples of critical intervals will be described below. Each time a value of a physiologic or demographic variable for the patient falls within a critical interval, scoring module 212 may record the occurrence of an event for the patient. Scoring module 212 may count the number of events for a patient over a time period, such as over a day. An output module 214 may generate, based on the count, output perceptible to a human user that indicates the patient's risk of mortality or likelihood of survival. For example, output module 214 may generate a graph that indicates a patient's score during a particular time interval. Output module 214 may transmit the graph or other indication to a physician. In one implementation, output module 214 may email a copy of the graph for a given patient to the patient's physician.

Also illustrated in FIG. 2 are model development module 216 and model validation module 218. Modules 216 and 218 may continuously update the variables used to generate the patient's scores and may update the statistical models associated therewith to improve predictive accuracy. A data archiving module 220 may archive data for patients for further model development or validation. A system monitor 222 monitors the overall activity of the system illustrated in FIG. 2.

Figure 3:
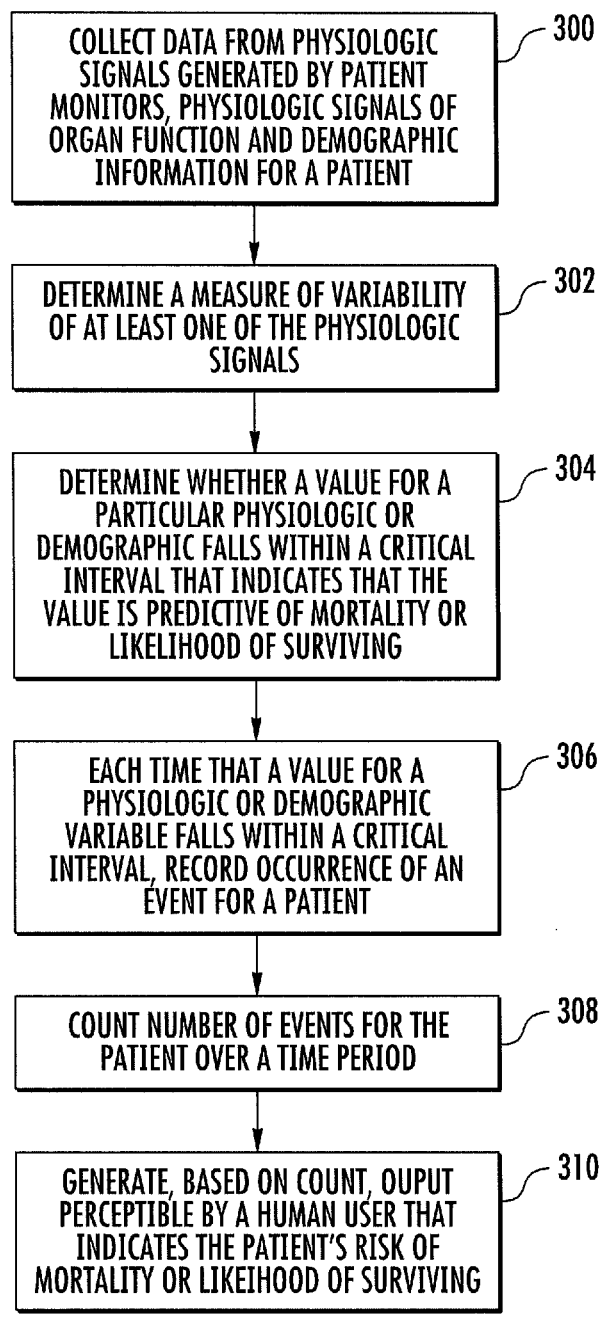
FIG. 3 is a flow chart illustrating exemplary steps for evaluating a hospital patient's risk of mortality according to an embodiment of the subject matter described herein.

FIG. 3 is a flow chart illustrating exemplary overall steps for evaluating a hospital patient's risk of mortality according to an embodiment of the subject matter described herein. Referring to FIG. 3, in step 300, data from physiologic signals generated by patient monitors, physiologic signals of organ function, and demographic information are collected for a patient. For example, as illustrated in FIG. 2, data collection module 200 may receive feeds from patient monitors and may also receive lab data and patient demographic information. In step 302, a measure of variability of at least one of the physiologic signals is determined. In FIG. 2, signal processing module 210 may compute derivatives of a signal's output from patient monitors as one measure of variability.

In step 304, it was determined whether a value for a particular physiologic or demographic variable falls within a critical interval that indicates that the value is predictive of mortality or likelihood of surviving. For example, scoring module 212 illustrated in FIG. 2 may determine whether a measured or calculated value for a variable for a patient falls within a range, referred to as a critical interval, where the range indicates that the patient is likely to die or to survive. In step 306, each time the value of for a physiologic or demographic variable falls within a critical interval, the occurrence of an event is recorded for the patient. For example, scoring module 212 may record the occurrence of events of an individual patient or an individual organ in a patient. In step 308, the number of events for a patient that occur within a time period is counted. For example, scoring module 212 may count the events for a particular patient over a time period, such as an hour or a day. In step 310, output perceptible by a human user is generated based on the counts. The output indicates the patient's risk of mortality or likelihood of surviving. For example, output module 214 illustrated in FIG. 2 may generate a graph or a table that indicates the number of events for a patient. This information may be delivered to the patient's physician so that the physician can determine whether intervention is needed.

As set forth above, one implementation of the subject matter described herein is referred to a REALTROMINS. REALTROMINS is a medical device that analyzes in real time 1) continuous ECG signals, 2) commonly analyzed serum lab tests, and 3) diagnosis and demographic related variables. These variables are input into advanced statistical algorithms where the values are compared to critical intervals to determine whether they indicate a patient is likely to die or to survive.

Time dimensioned transformations using this information included aggregating all raw data into a common time frequency as HRV information exist in both sub-seconds and within a set of 128 beats while lab tests are intermittent based upon physician requests. First and second order derivatives, centered moving averages and standard deviations are calculated with the goal of data mining to construct a mathematical algorithm that captures viable representations of existing phenomena hidden within this database. Using QTMS V4—Optimized Binning, a series of SAS Macros, critical intervals found with the total distribution of each variable were calculated. These bins are selected based upon their ability to lift the mortality rate from the base. This is done to focus attention onto those specific ranges with significantly increased mortality rates and represent them as a binary inclusionary condition. These viable representations must be sufficiently robust, based upon their "parameter-estimation," so as to repeat any predicted classification onto an independent hold out sample. Different classes of algorithms were found within SAS-EM5.3 (Statistical Analysis Systems, Cary N.C. USA) ranging from standard regression, to rule induction, and several neural networks.

One aim of the subject matter described is to provide REALTROMINS bioinformatics systems for use in hospitalized children (PICU) in the ICU and Peds Rapid Response (RR).

Classes of variables in REALTROMINS.

The following classes of variables may be used by the system illustrated in FIG. 2 to evaluate a patient's risk of mortality.

1) Continuous physiologic signals (i.e. electrocardiogram (ECG));
2) Advanced measures of variability of the physiologic signal (i.e. power spectral analysis);
3) Physiologic based measures of organ function important in predicting mortality (i.e. serum glucose) and measures of their variability; and
4) Demographic (i.e. age) and diagnosis related (i.e. postoperative status) predictors of mortality.

Specific Data Elements.

The following physiologic based measures of organ function may be used by the system illustrated in FIG. 2 to evaluate a hospital patient's risk of mortality.

Fluids: sodium, potassium, glucose, urea nitrogen, creatinine, ionized calcium, magnesium, phosphorus, whole blood glucose measurements, urine output, fluids administered (IV and/or enteral), weight;

Hematologic: hemoglobin, platelet count, prothrombin time-INR, partial thromboplastin time, D-dimers;

Hepatic: bilirubin, transaminases, albumin, total protein, amylase, lipase;

Cardiac: heart rate, noninvasive blood pressure (systolic and diastolic)#, troponin, CK-MB, lactate level;

Respiratory: rate, pH, PC02, P02, HC03, 02 saturation via pulse oximetry, fractional inspired oxygen;

Neurologic: Glasgow coma score, pain score; and

Immunologic: temperature, white cell count, absolute neutrophil and lymphocyte count, c reactive protein.

Demographic and Diagnosis Related Predictors:

The following demographic variables may be used by the system illustrated in FIG. 2 to evaluate a hospital patient's risk of mortality.

1) Age; 2) General diagnostic groups (i.e. oncologic disease); and 3) Other (nursing acuity score, therapeutic intervention score, etc.

One previous version of REALTROMINS that did not use critical intervals has been in operation since July 2008 and has expanded to include all 130 beds in the NC Children's Hospital. In addition, all of the low resolution data streams from the entire 729 bed adult hospital (excluding the monitor waveform and numeric data) are now accessible to our research environment. Since July 2008, over 2,400 pediatric patient records have been fully acquired, processed, and archived. Uniquely, the system is created and optimized for real-time clinical decision support research, unlike conventional clinical information systems, that are either geared towards clinical operations or retrospective data collection and review. This feature is critical for understanding and overcoming production constraints on clinical decision support research.

Figure 4A:
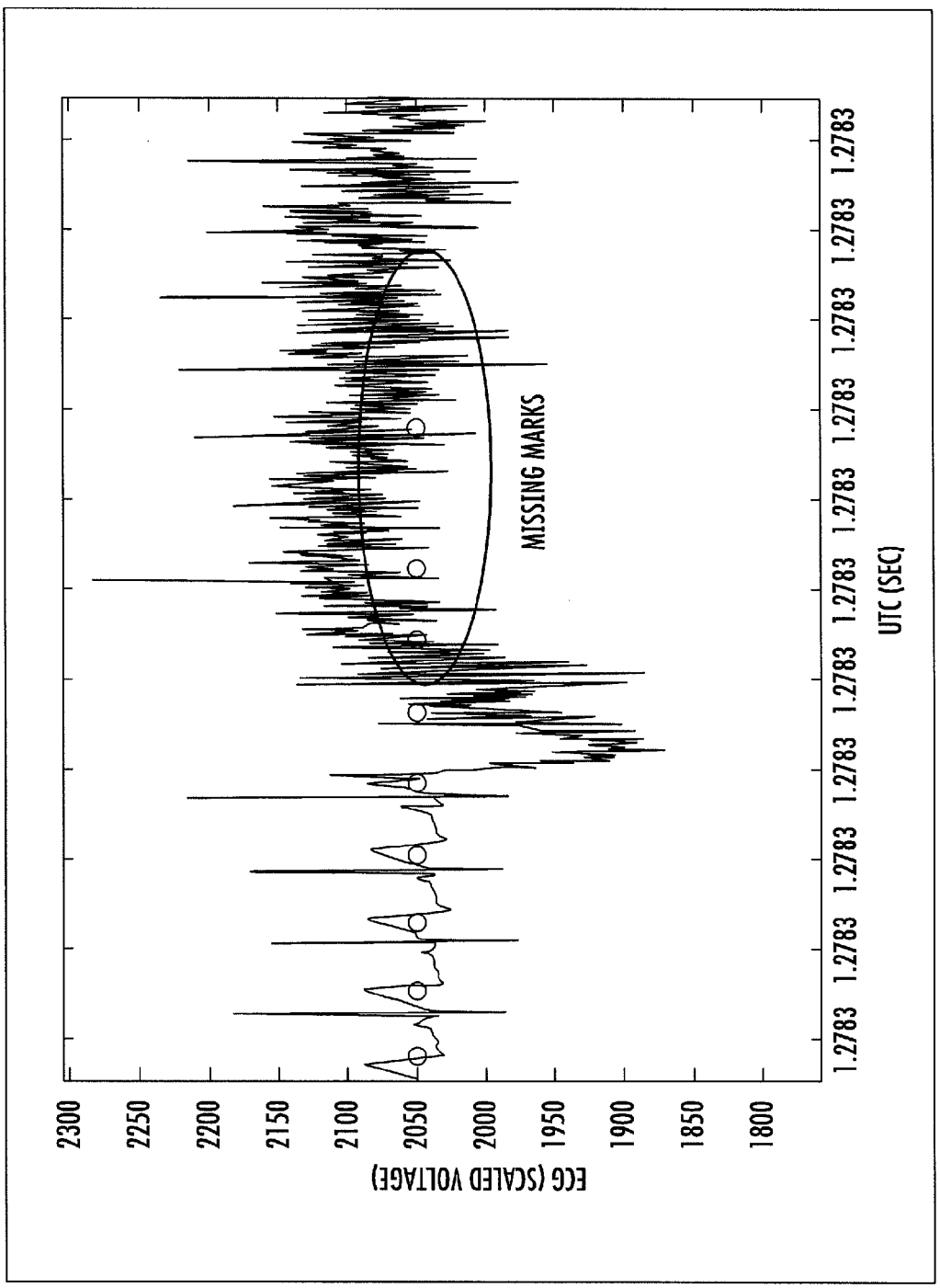
FIGS. 4A and 4B are graphs of ECG voltage versus time that may be analyzed by the system illustrated in FIG. 2 to evaluate a patient's risk of mortality according to an embodiment of the subject matter described herein.
Figure 4B:
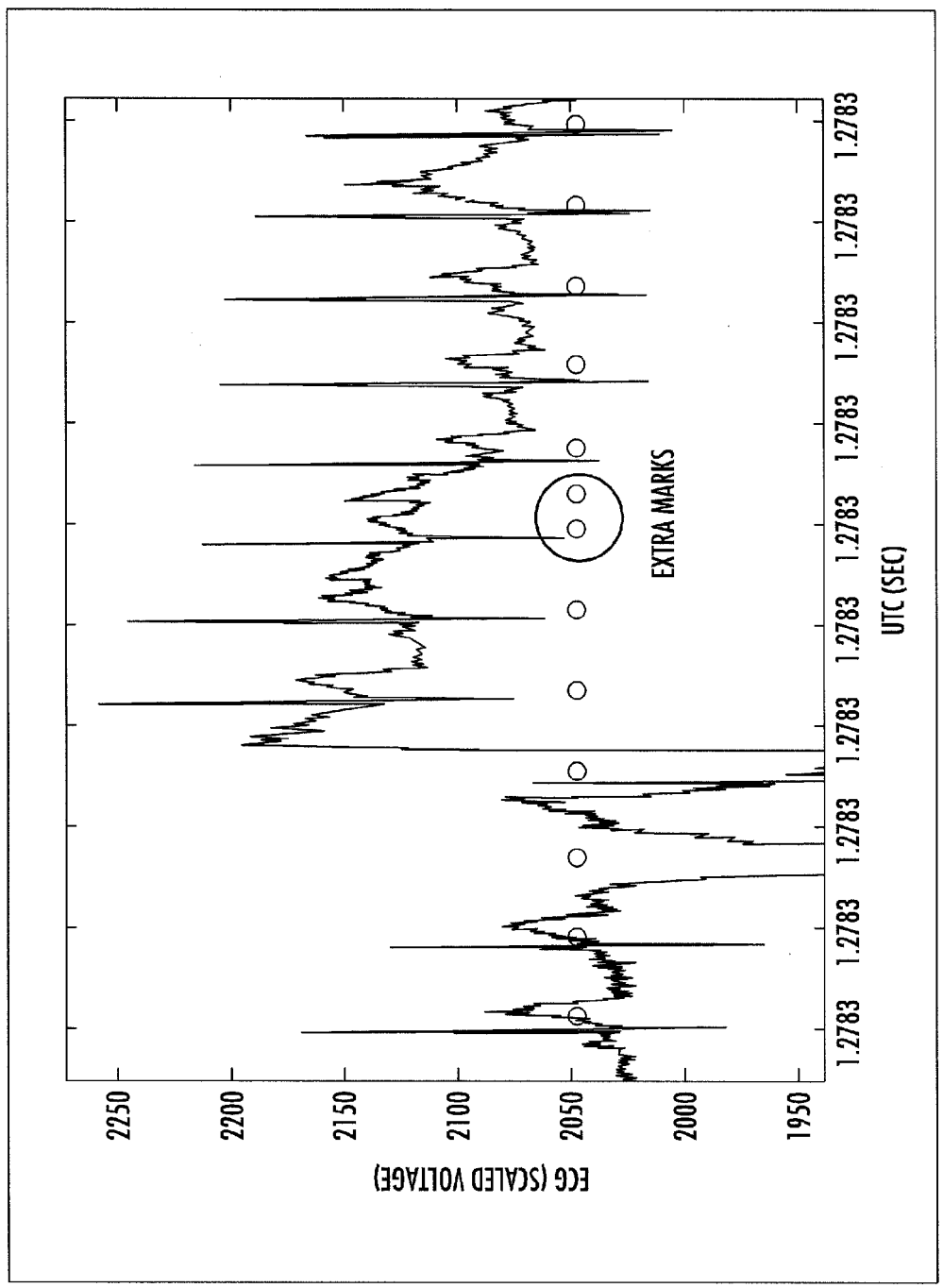

Continuous ECG Data: Streaming ECG Data was captured at 224 data points per second tagged with a UTC millisecond time stamp provided by the ICU monitoring system (SpaceLabs Medical). To create time-domain variables, the R peaks (fiducial point) had to be accurately identified. While the monitoring system has an analog process for estimating the location of R peaks, this process does not always identify the correct number or location of the R peak. FIGS. 4A and 4B illustrate the raw ECG signal with peaks marked using SpaceLabs algorithms.

Stripping out the actual Rpeak time stamp and then counting binned-values of the time difference between peaks in increments of 100 milliseconds calculated time domain variables. While current research had focused only on the pNN50 value we found significance elsewhere among the range of this distribution. Significance was found among different lags, e.g., pNN700, pNN800, and pNN400. FIGS. 5A and 5B are tables illustrating means and standard deviations for pNNXXX distributions (dead1=arrested, 0=alive). From the NN interval data (time between successive R waves), SDNN (standard deviation of the NN (consecutive normal sinus intervals), RMSSD (root mean square successive difference), NN50 (the number of NN intervals with differences >50 ms), pNN50 (the proportion of NN50 intervals divided by the total NN intervals), pNNx series (where is x=time>0 ms), NN range, coefficient of variation, and the min/max heart period for each 128 beat minor time epoch are calculated.

Spectral data was extracted by stripping on the fixed 64 records for each group of records. Frequency bands were grouped as follows using the interpolated heart rate spectra values to calculate area within that specific band of frequencies. These frequencies corresponded to the ultra-low frequency (ULF), very low frequency (VLF), low frequency (LF), and high frequency (HF) bands.

Transformations were performed upon the interpolated heart rate spectra values to convert them into variance. The variance present in the HR data is obtained from the power spectrum according to methods described in Bendat J S, Piersol A G. Engineering Applications of Correlation and Spectral Analysis. 2nd Edition. New York: John Wiley & Sons, Inc.; 1993, the disclosure of which is incorporated herein by reference in its entirety. Since our HR data was normalized, the mean is zero, and the sum of the power in the frequency bands is directly equal to the variance. We chose to generate our spectra using the HR time series data in a similar manner to methods used by Pomeranz B, MacAulay R, Caudill M. Assessment of autonomic function in humans by heart rate spectral analysis. *Am J Physiol* 1985; 248:H151-3, the disclosure of which is incorporated herein by reference in its entirety. Because we use the normalized HR data and not the heart beat period time series, our units of power are bpm2/bpm2 (unitless) as opposed to ms2 or normalized units reported by some other investigators. The value for power reported within each frequency band will vary, depending on the units, but the ratios of interest (e.g. low frequency power to high frequency power, LF/HF) will not be affected. FIGS. 6A and 6B are tables illustrating means and standard deviations from spectral distributions where dead 1=arrested, 0=alive.

It can be seen from FIGS. 6A and 6B that the standard deviations exceed the means indicating nonlinear distributions. Using QTMS optimal bins, critical intervals were developed by isolating specific sub-ranges within the total distribution of each variable. They are color coded by importance in identifying dead patients by focusing attention to cut points masked by the means. Standard means testing focuses on values of 0.54 for the dead while the extreme bin below 0.34 indexes at 344. This approach is used on every variable to recode new variables with significant lift. FIG. 7 is a table illustrating critical intervals used by the system illustrated in FIG. 2 to evaluate a patient's risk of mortality. In FIG. 7, intervals 1 and 2 may be classified as critical intervals because they have mortality rates of 47.63 and 20.53%, respectively. While not accurately predictive of mortality alone, a variable that falls in intervals 1 and 2 can be considered in a model with other variables that can be highly predictive of a patient's risk of mortality. Exemplary models that combine variables will be set forth in detail below.

Eight additional transformations to each raw variable were also created and include centered moving averages, centered moving standard deviations nested across first and second order derivatives in attempts to provide information on how these values change over the course of each patient's stay. FIGS. 8A and 8B illustrate transformable variables that may be used by the system illustrated in FIG. 2 to predict a hospital patient's risk of mortality.

Physiologic based measures of organ function important in predicting mortality were defined by a battery of 96 laboratory and streaming physiological tests collected during the patients' stay in the PICU. These tests were collected based upon clinical need which varied by patient and varied over time within patient. This was accomplished by looking within each variable's distributions and identifying intervals that index high against base-mortality using the optimized binning procedure found within QTMS V4.0 and previously described. This procedure was also performed on the eight additional transformations for each variable (centered moving averages, standard deviation on first and second derivatives). FIGS. 9A and 9B illustrate tables that contain laboratory tests that are available for evaluating a hospital patient's risk of mortality.

The basic idea is to find intervals within the total distribution where the target distribution (arrested patients) occurs in different percentages. The output found below helps identify these intervals by first binning the entire distribution into deciles or 10 equaled sized partitions. These intervals are used to calculate a mortality rate within that range and index it to the overall mortality rate. The table below displays those intervals where the index is greater than 120. From the 98 raw labs and streaming physiologic data, over 500 composite and transformed variables were reported on with 2,400 intervals from that set indexing 120+. FIGS. 10A and 10B are tables illustrating composite and transformation variables that may be used by the system illustrated in FIG. 2 to evaluate a hospital patient's risk of mortality. FIGS. 11A and 11B are tables illustrating critical intervals for the variables of FIGS. 10A and 10B that may be used to evaluate a hospital patient's risk of mortality.

Figure 12A:
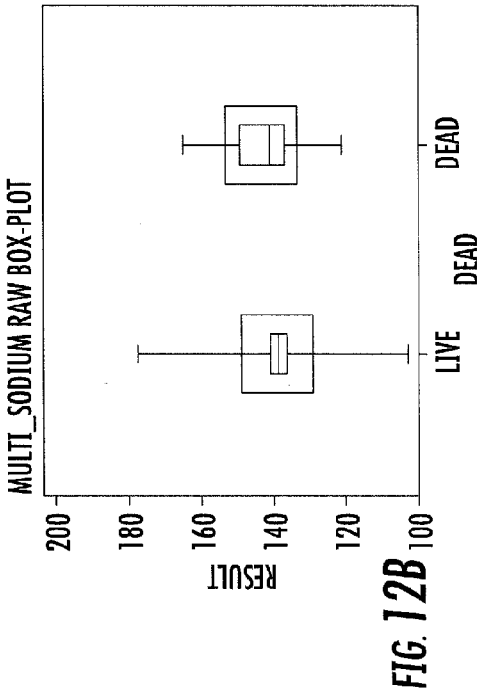
FIG. 12A is a table.
Figure 12B:
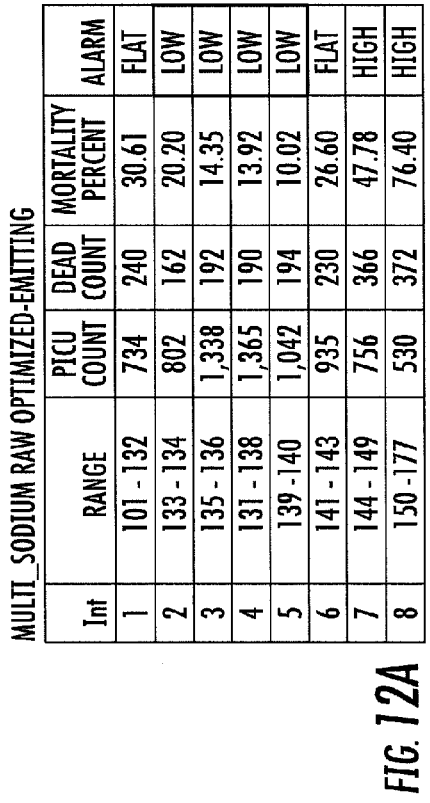
FIG. 12B is a graph illustrating critical intervals for live and dead patients for a particular variable that may be used by the system illustrated in FIG. 2 to evaluate a patient's risk of mortality according to an embodiment of the subject matter described herein.
Figure 13B:
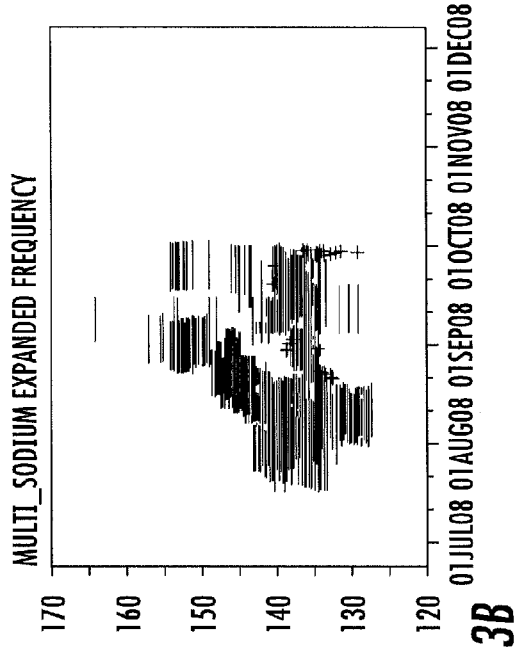
FIGS. 13A and 13B are plots of sodium frequency versus time for a given patient according to an embodiment of the subject matter described herein.
Figure 13A:
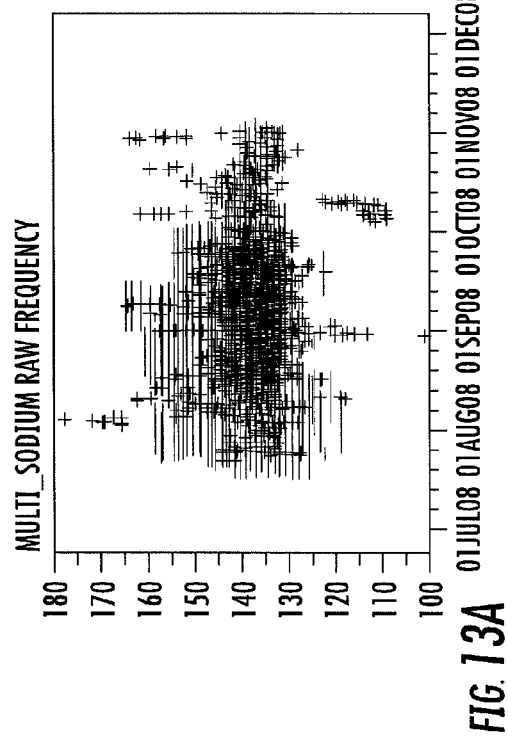
Figure 14A:
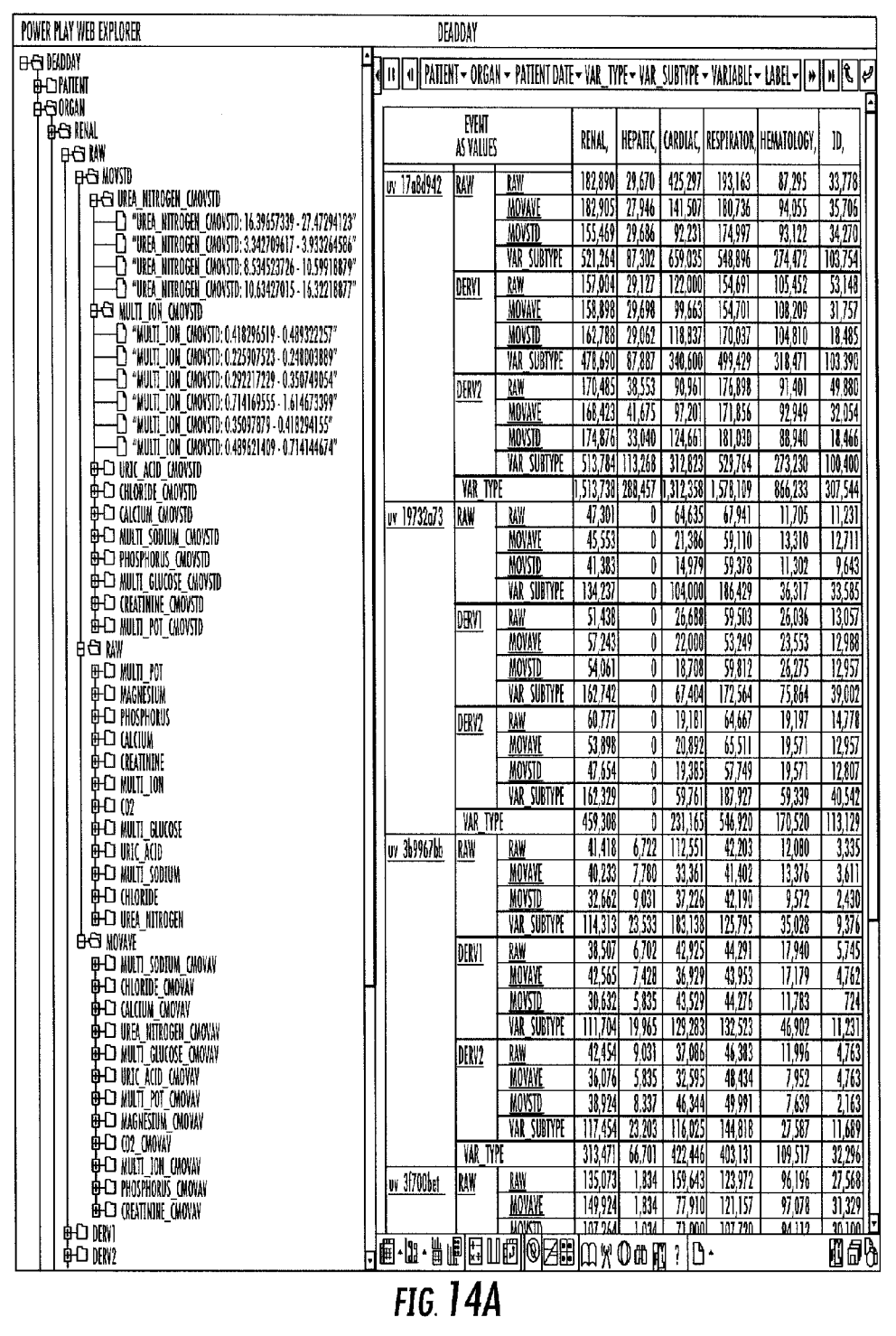
Figure 14B:
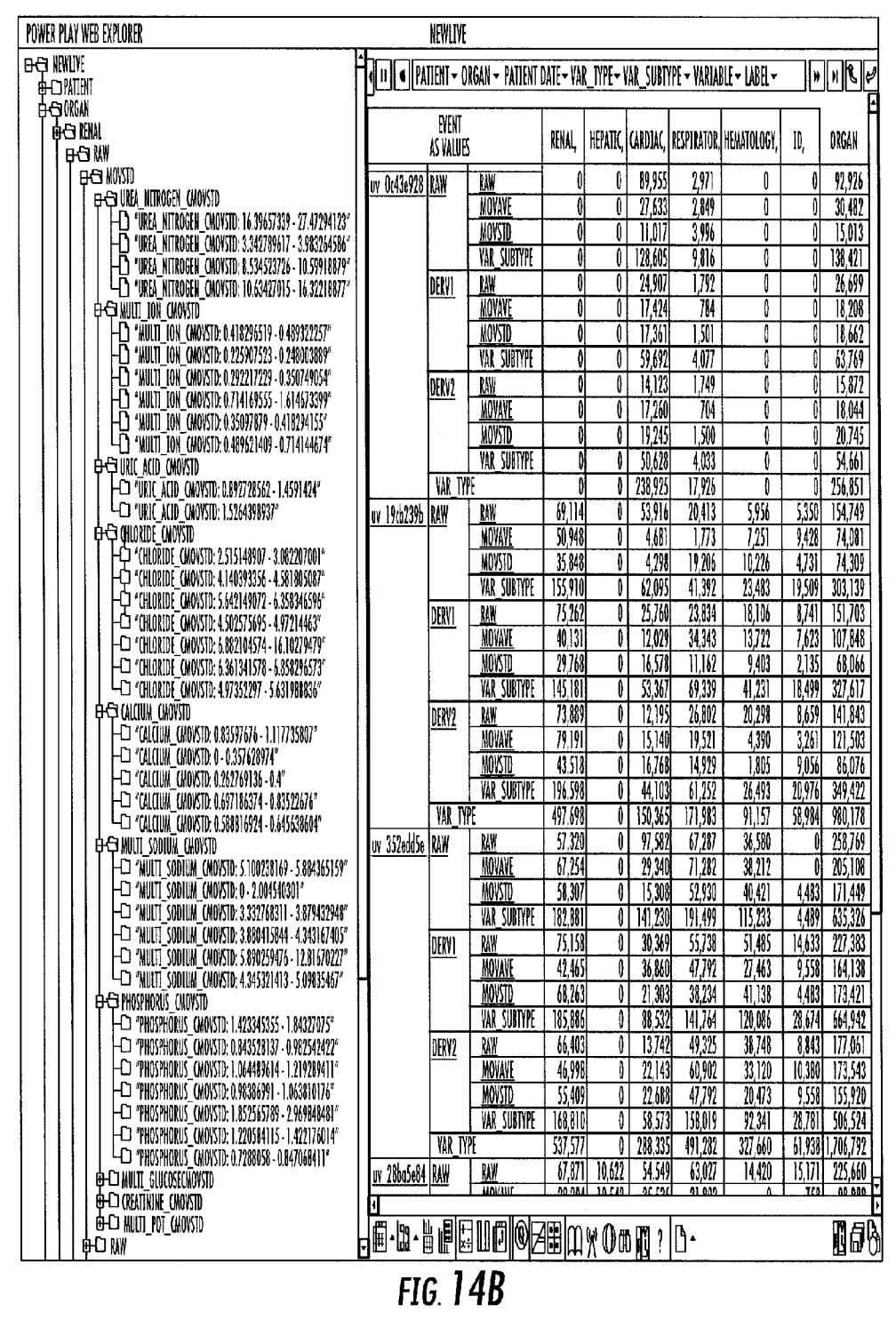
Figures 15A, 15B:
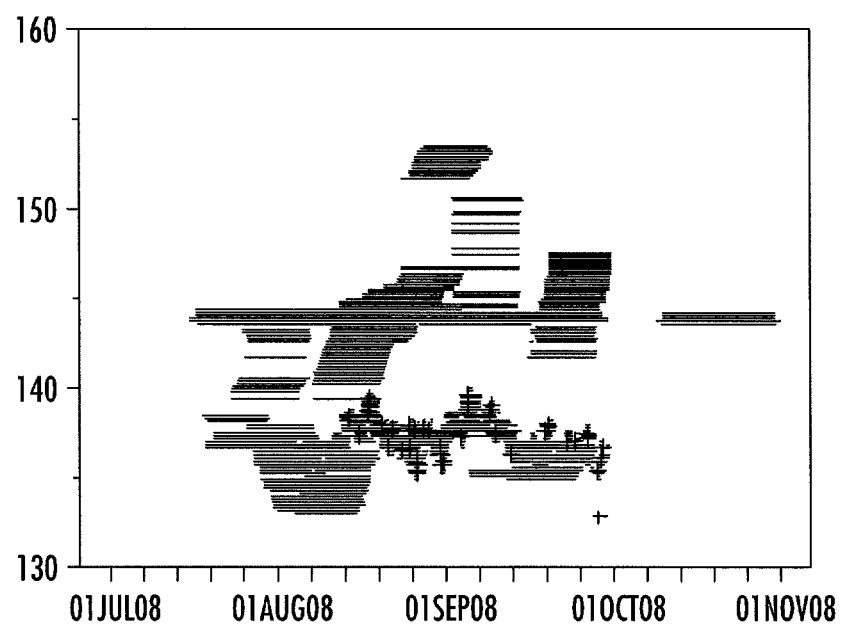
FIG. 15A is a table.
FIG. 15B is a graph illustrating critical intervals of a particular variable that may be used by the system illustrated in FIG. 2 to evaluate a patient's risk of mortality according to an embodiment of the subject matter described herein.
Figures 15C, 15D:
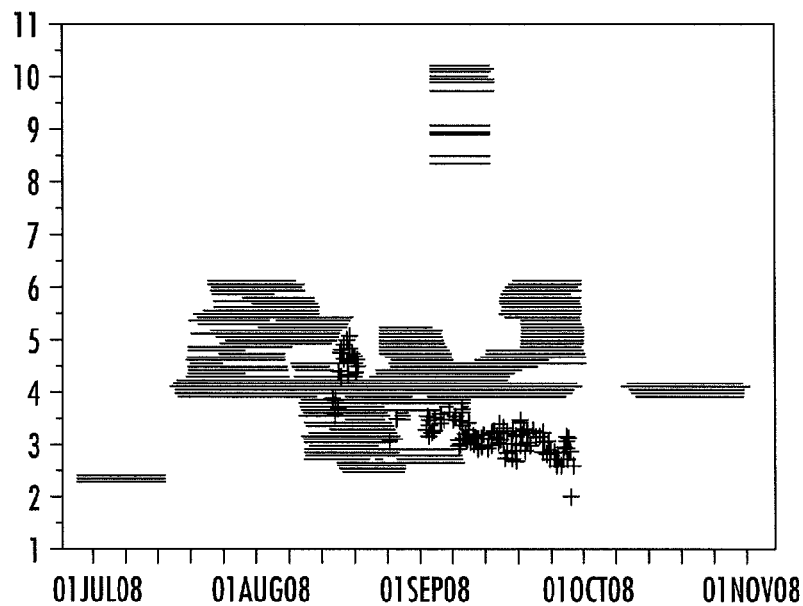
FIG. 15C is a table and FIG. 15D is a graph of critical intervals for a particular variable that may be used by the system illustrated in FIG. 2 to evaluate a patient's risk of mortality according to an embodiment of the subject matter described herein.

The advantage to using these quantitatively derived intervals is that any means of testing tends to focus attention on incorrect areas within the total distributions when the data is not normally distributed. A t-test for Sodium compares a mean of 141 for live patients versus 137 for arresting patients. You find flat indexes about those values in the graphic below. The data is not normal but skewed. By recoding the green intervals into a (0,1) we intensify the strength of the effect. We also have an advantage in that we can now include patients that did not have any test by coding them as a 0. FIGS. 12A and 12B are respectively a table and a graph of critical intervals for sodium content of live and dead patients. FIGS. 13A and 13B are graphs of sodium frequency versus time. FIGS. 14A-14C illustrate event counts for different organs for different patients. FIGS. 15A-15D illustrate critical intervals that may be used by the system illustrated in FIG. 2 for evaluating a patient's risk of mortality. The critical intervals in FIGS. 15A-15D may be determined using a single factor scan procedure found with QTMSV3.2 profiling for extreme derogatory ranges within the battery of lab tests.

Figure 16A:
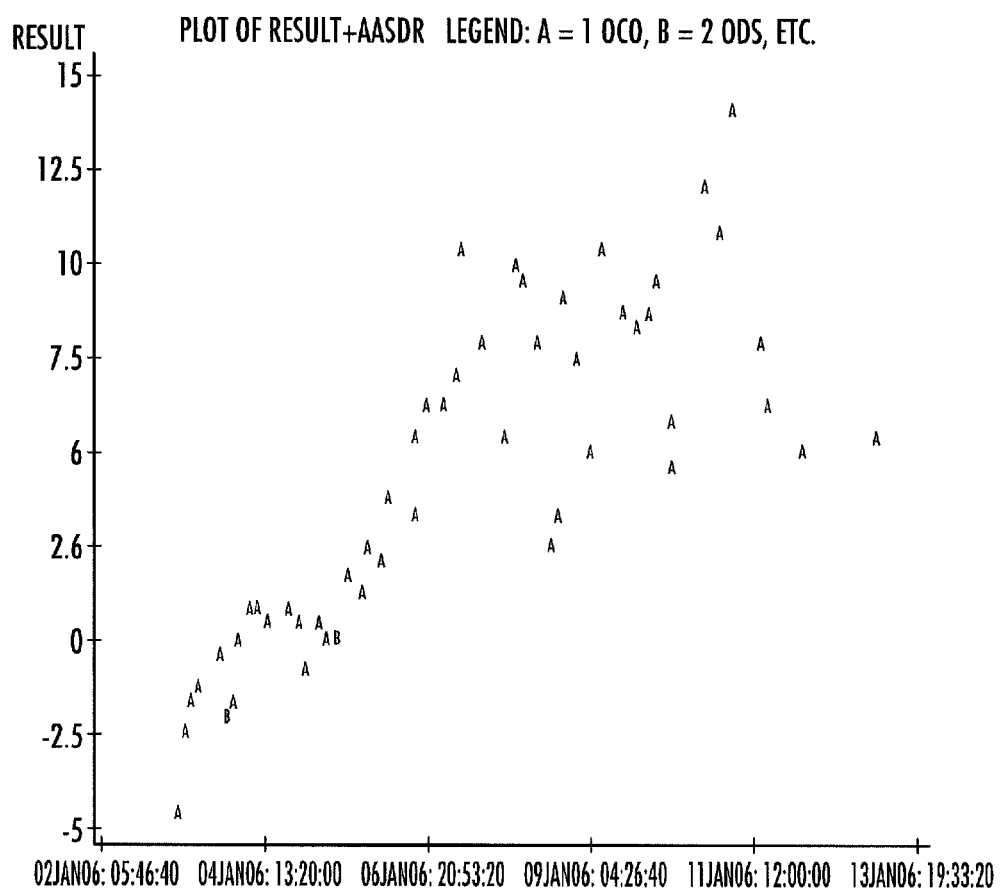
FIG. 16A is a graph of intermittent raw data.
Figure 16B:
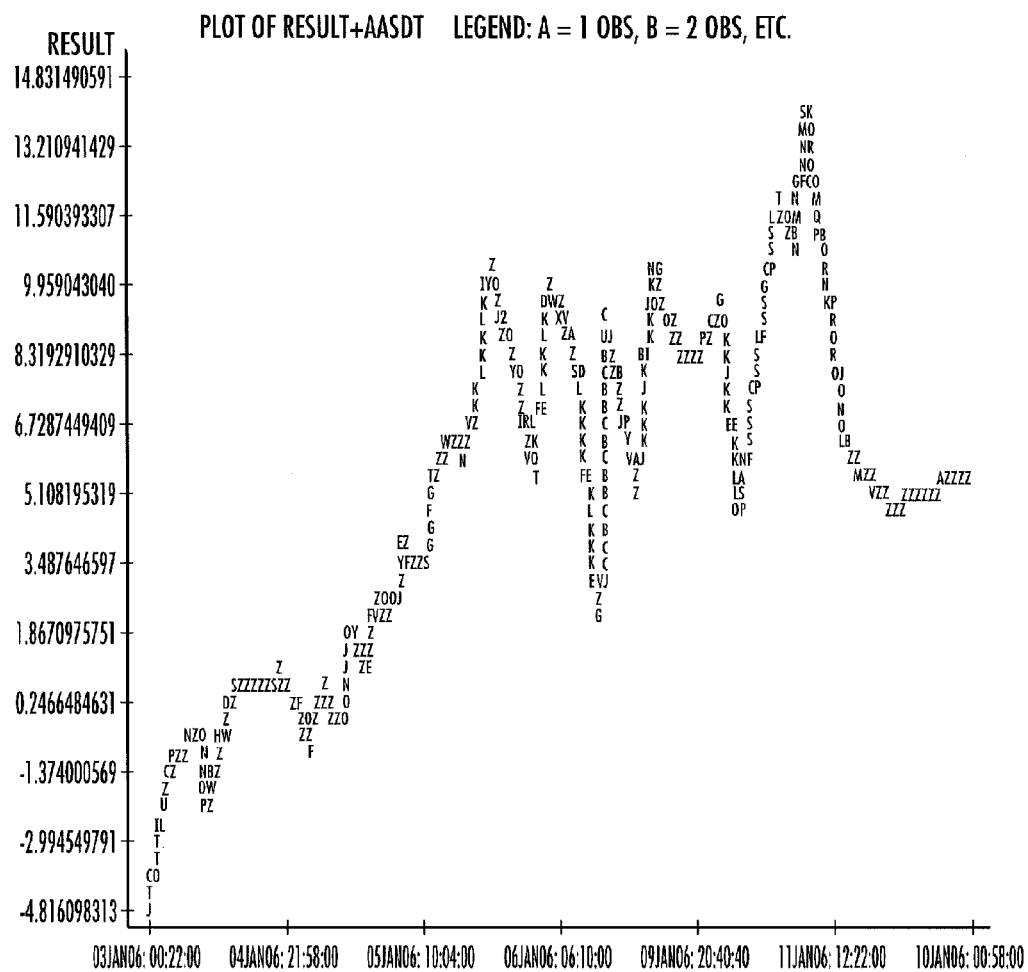
FIG. 16B is a graph of extrapolated data in 2 minute increments which calibrates all data into exact 2minute intervals.

Developing a Common Time Hierarchy. This study was an accumulation of patient data collected continuously during the PICU hospitalization. The units of time for each grouping of variables were different. The units for the time domain variables were sub-second differences between R peaks, while the time span represented in the frequency domain was based on 128 bpm). Finally the units for intermittent variables were logged at the actual clock time taken. To join these 4 groups of data, it was determined to put this information into a common time frame of 2 minutes. This was accomplished using SAS procedure Expand (part of the ETS Suite within SAS) which can combine time series with different frequencies using various interpolative methods that can be used to convert raw data into a higher frequency series or aggregate down to a lower frequency series. FIGS. 16A and 16B illustrate raw and extrapolated data generated using the procedure Expand. FIG. 16A illustrates intermittent original data and FIG. 16B illustrates extrapolated data into increments.

Following these procedures, we extrapolated all data from all sources, calibrated into 2 minute epochs for all patients. This resulted in an analytic data set of 1,000,000 two minute records that contain the 500+ variables and transformations described before. Each packet represents two minutes of clock time with information from the pNN category, spectral information, and derogatory markers from the lab tests and demographics collected.

In conclusion, we have taken data from disparate sources and collected along difference time increments and built an integrated single source analytic file all calibrated into two minute increments.

To answer issues about overfitting and the fact that many of these critical intervals are correlated, an added step was performed with the NICU model which was to reduce the number of intervals by various rank reduction techniques (PCA) and model using the factor scores. Because each factor score is continuous, a Two-Group Multiple Discriminant was used and is reported.

Multivariate Model Building: The composite file described above was analyzed using SAS Enterprise Miner 5.3 with the logistic regression model yielding absolute best fit among several close alternatives. All data through December 2009 yielded a file of 750,000 2 minute packets each containing the 500+raw and transformed variables along with the 2,400 optimized bins (based upon the critical intervals among these 500+variables). A 40% training sample (304,929 packets) was used to model build with a 30% validation sample (228,696 packets) and a 30% test sample (228,698 packets) held out. The summary of all samples is provided below.

Training Sensitivity=38,739/(38,739+3526)=91.65%
Training Specificity=261,586/(261,586+1078)=99.58%
Validation Sensitivity=29,063/(29,063+2636)=91.68%
Validation Specificity=196,107/(196,107+890)=99.54%

The testing sample produced identical results as the validation sample concluding the model is robust.

Conclusions indicate correctly NOT alarming LIVE patients 99% of the time and correctly alarming DEAD patients 91% of the time during the entire course of their PICU stay. Conversely the model misses a DEAD packet 9% of the time. While this represents each 2 minute result, accumulating signals over the course of 30 minutes to 1 hour would yield a clearer picture and a better summarization of the patient's current status.

Figure 17A:
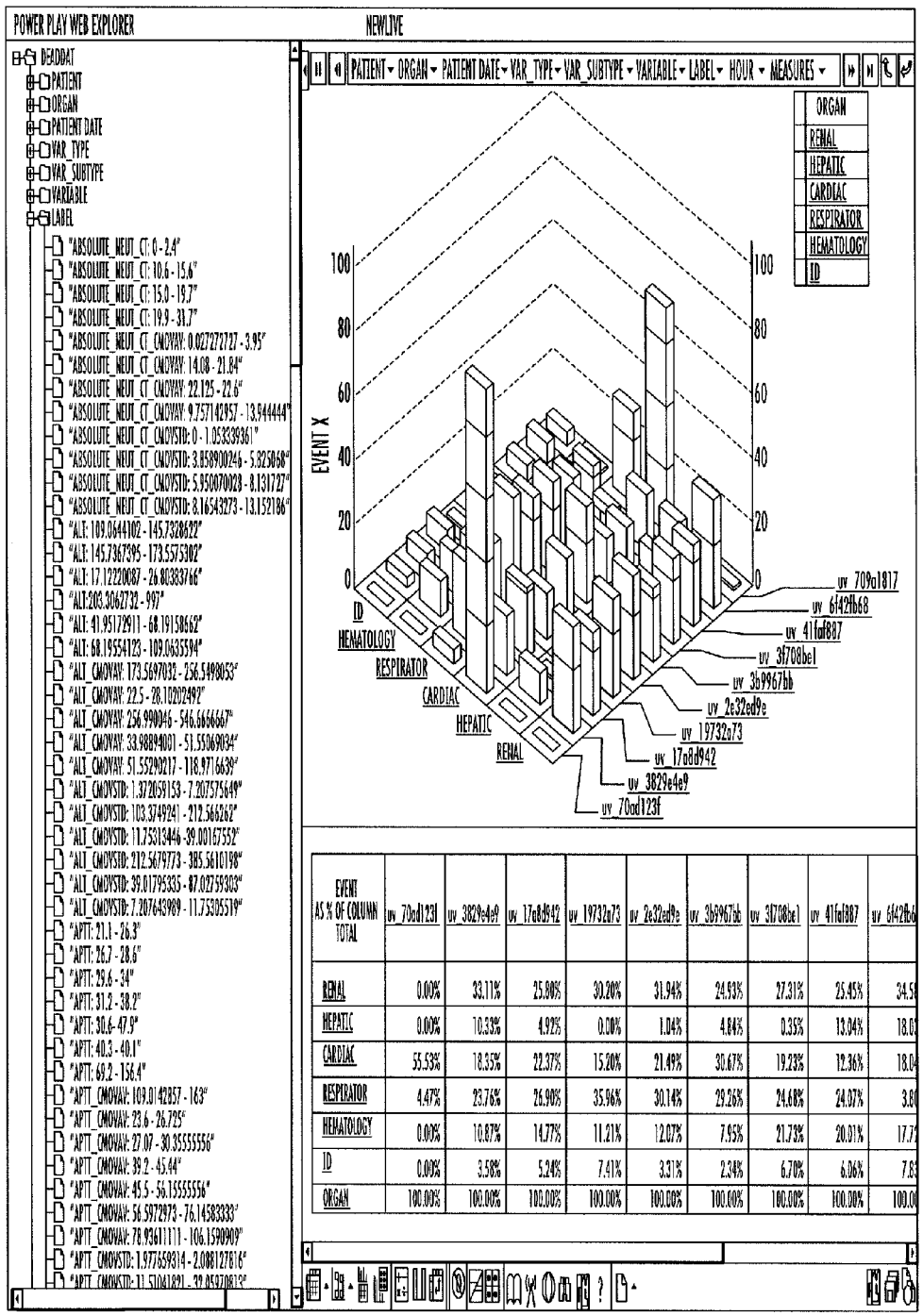
FIG. 17A is a graph of patient event counts per organ and FIG. 17B is a table of the same data that may be generated by the system illustrated in FIG. 2 according to an embodiment of the subject matter described herein.
Figure 17B:
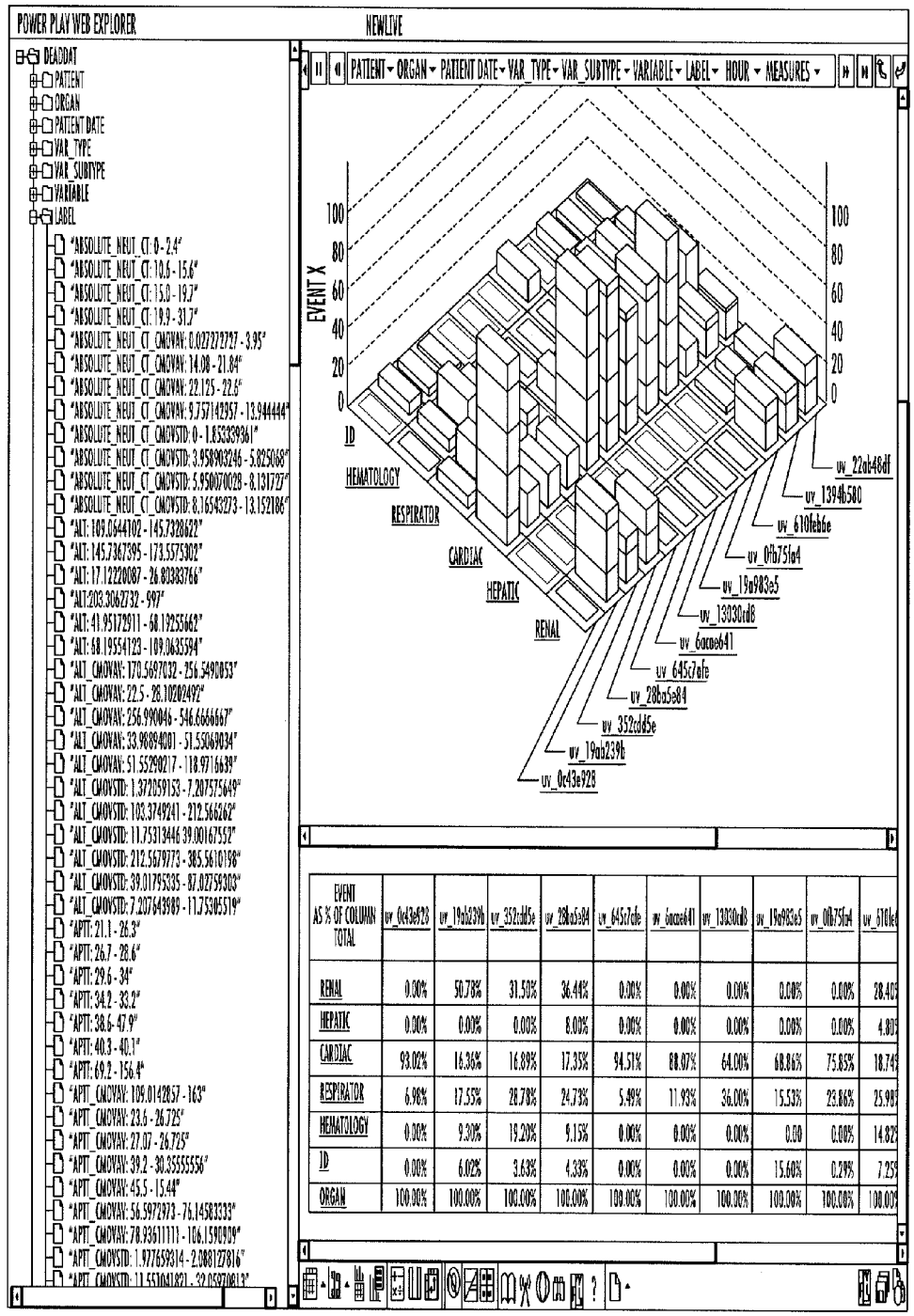

Interactive Reporting: As we collect new patient information and process it through the same algorithms just described, using COGNOS data management software available from IBM corporation and this test model, REALTROMINS risk of mortality score with a drill down of the individual components contributing to that score will be provided in real time allowing for diagnostic updates every 2 minutes. FIG. 17A is a graph and FIG. 17B is a table illustrating exemplary scores that may be generated for a patient. The scores may be presented on a per-organ and/or per-patient basis. Such scores may be emailed to a physician in graphical format or in tabular format to allow the physician to make a quick evaluation of the patient's risk of mortality.

Information visualization is to present significant and non-obvious patterns within these vast high-dimensional datasets and provide users with intuitive interface in their exploratory analysis. Many salient patterns may be only visible in subspaces of the data. Dimensionality reduction and clustering have become an effective approach to capture and organize these patterns, aid in the removal of irrelevant or redundant information, and enhances the comprehensibility of the whole dataset.

In this project, each patient is monitored continuously and a high-dimensional feature vector is derived for every 2-minute long interval. A method to organize and summarize these feature vectors so that a user can navigate through them easily is desirable. In order to generate a consistent yet succinct view of all data, we need to establish and evaluate the relationships between these feature vectors. Given the pairwise relationships between feature vectors, a representation that can efficiently organize them is needed. This includes the ability to group and summarize similar vectors and the ability to allow users to examine the relationship between feature vectors and/or groups of feature vectors at various resolutions seamlessly. Ideally, we want to derive plausible hierarchical categorizations of feature vectors from their pairwise dissimilarities. We plan to project these high dimensional vectors onto some low dimensional space and apply hierarchical clustering.

We have continued to improve upon our existing reporting technologies imbedded in REALTROMINS. Exemplary unconventional and exceptionally innovative aspects to our approach are listed below:

streaming real time continuous physiologic data for the entire length of ICU hospitalization;

interfacing multiple disparate forms of clinically important patient data into a common database for research development of an advanced bioinformatics system;

providing an informatics system storing high and low resolution data to readily allow for frequent recalibrations of the predictive models;

providing mortality predictions based on statistical principles, but utilizing novel critical interval based techniques;

providing a real time continuously updated risk of morality assessment across a broad spectrum of patients; and providing a graphical interface that allows bedside care givers to understand and act upon large sets of clinically important data.

As set forth above, one aspect of the subject matter described herein uses a model that includes critical intervals for multiple variables to which monitored values for a patient are compared in order to generate an indication of the patient's risk of mortality. The following is an example of a NICU model that may be implemented by the system illustrated in FIG. 2 to evaluate a patient's risk of mortality:

| Variable | 0 | 1 |
|---|---|---|
| Constant | −0.20091 | −6.81060 |
| Factor 1 | −0.28830 | 1.65814 |
| Factor 2 | 0.00604 | −0.00391 |
| Factor 3 | −0.01189 | 0.07554 |
| Factor 4 | −0.69595 | 4.07369 |
| Factor 5 | −0.28752 | 1.66290 |
| Factor 6 | −0.26048 | 1.52776 |
| Factor 7 | −0.08562 | 0.47352 |
| Factor 8 | −0.20929 | 1.24321 |
| Factor 9 | −0.21608 | 1.25133 |
| Factor 10 | −0.13746 | 0.80579 |
| Factor 11 | −0.15405 | 0.90698 |
| Factor 12 | −0.06925 | 0.38799 |
| Factor 13 | −0.09913 | 0.57833 |
| Factor 14 | −0.08711 | 0.53104 |
| Factor 15 | −0.08240 | 0.53599 |
| Factor 16 | −0.12089 | 0.71464 |
| Factor 17 | −0.09577 | 0.54900 |
| Factor 18 | −0.14158 | 0.82108 |
| Factor 19 | −0.13160 | 0.74267 |
| Factor 20 | −0.13613 | 0.80762 |
| Factor 21 | −0.08358 | 0.51459 |
| Factor 22 | −0.06739 | 0.41867 |
| Factor 23 | −0.10166 | 0.60537 |
| Factor 24 | −0.18174 | 1.05345 |
| Factor 25 | −0.23663 | 1.36195 |
| Factor 26 | −0.01213 | 0.10820 |
| Factor 27 | 0.05107 | −0.29622 |
| Factor 28 | −0.14207 | 0.78863 |
| Factor 29 | −0.06722 | 0.40433 |
| Factor 30 | −0.06454 | 0.38491 |
| Factor 31 | −0.07605 | 0.42829 |
| Factor 32 | −0.11187 | 0.67386 |
| Factor 33 | −0.03017 | 0.13137 |
| Factor 34 | −0.01941 | 0.13086 |
| Factor 35 | −0.02694 | 0.14742 |
| Factor 36 | −0.03483 | 0.18450 |
| Factor 37 | −0.04668 | 0.29202 |
| Factor 38 | −0.03601 | 0.20023 |
| Factor 39 | 0.05874 | −0.31724 |
| Factor 40 | −0.06479 | 0.39679 |
| Factor 41 | −0.09578 | 0.55065 |
| Factor 42 | −0.07738 | 0.45175 |
| Factor 43 | −0.05947 | 0.30176 |
| Factor 44 | −0.16494 | 0.96125 |
| Factor 45 | −0.04428 | 0.24945 |
| Factor 46 | −0.02387 | 0.15645 |
| Factor 47 | −0.05996 | 0.33865 |
| Factor 48 | −0.10723 | 0.61003 |
| Factor 49 | −0.03515 | 0.18770 |
| Factor 50 | −0.02083 | 0.15172 |
| Factor 51 | −0.04029 | 0.22747 |
| Factor 52 | −0.06045 | 0.36015 |
| Factor 53 | −0.04780 | 0.30002 |
| Factor 54 | −0.07062 | 0.39624 |
| Factor 55 | −0.07177 | 0.41246 |
| Factor 56 | −0.05444 | 0.29256 |
| Factor 57 | −0.05473 | 0.35851 |
| Factor 58 | −0.05819 | 0.36887 |
| Factor 59 | −0.05257 | 0.29494 |
| Factor 60 | −0.04006 | 0.25405 |
| Factor 61 | −0.05685 | 0.28521 |
| Factor 62 | −0.05115 | 0.29318 |
| Factor 63 | −0.05635 | 0.34883 |
| Factor 64 | −0.06668 | 0.39700 |

-continued

| Variable | 0 | 1 |
|---|---|---|
| Factor 65 | −0.06095 | 0.36169 |
| Factor 66 | −0.05292 | 0.28978 |
| Factor 67 | −0.04499 | 0.21666 |
| Factor 68 | −0.00444 | 0.01509 |
| Factor 69 | −0.04559 | 0.23776 |
| Factor 70 | −0.04526 | 0.26049 |
| Factor 71 | −0.11500 | 0.65056 |
| Factor 72 | −0.03565 | 0.19519 |
| Factor 73 | −0.04075 | 0.22143 |
| Factor 74 | −0.03697 | 0.21035 |
| Factor 75 | −0.03543 | 0.21661 |
| Factor 76 | −0.04793 | 0.27253 |
| Factor 77 | −0.05694 | 0.29992 |
| Factor 78 | −0.08618 | 0.50202 |
| Factor 79 | −0.03524 | 0.20943 |
| Factor 80 | −0.04470 | 0.24862 |
| Factor 81 | −0.05235 | 0.29493 |
| Factor 82 | −0.07565 | 0.44194 |
| Factor 83 | −0.03100 | 0.18079 |
| Factor 84 | −0.04348 | 0.25106 |
| Factor 85 | −0.05120 | 0.28331 |
| Factor 86 | −0.03110 | 0.18381 |
| Factor 87 | −0.03059 | 0.15312 |
| Factor 88 | −0.04195 | 0.21911 |
| Factor 89 | −0.02403 | 0.13863 |
| Factor 90 | −0.03540 | 0.18019 |
| Factor 91 | −0.08765 | 0.51857 |
| Factor 92 | −0.04127 | 0.22865 |
| Factor 93 | −0.01852 | 0.13274 |
| Factor 94 | −0.04286 | 0.24996 |
| Factor 95 | −0.00759 | 0.01358 |
| Factor 96 | −0.06443 | 0.35972 |
| Factor 97 | −0.03615 | 0.15639 |
| Factor 98 | −0.04045 | 0.25249 |
| Factor 99 | 0.00357 | −0.03108 |

Figure 17C:
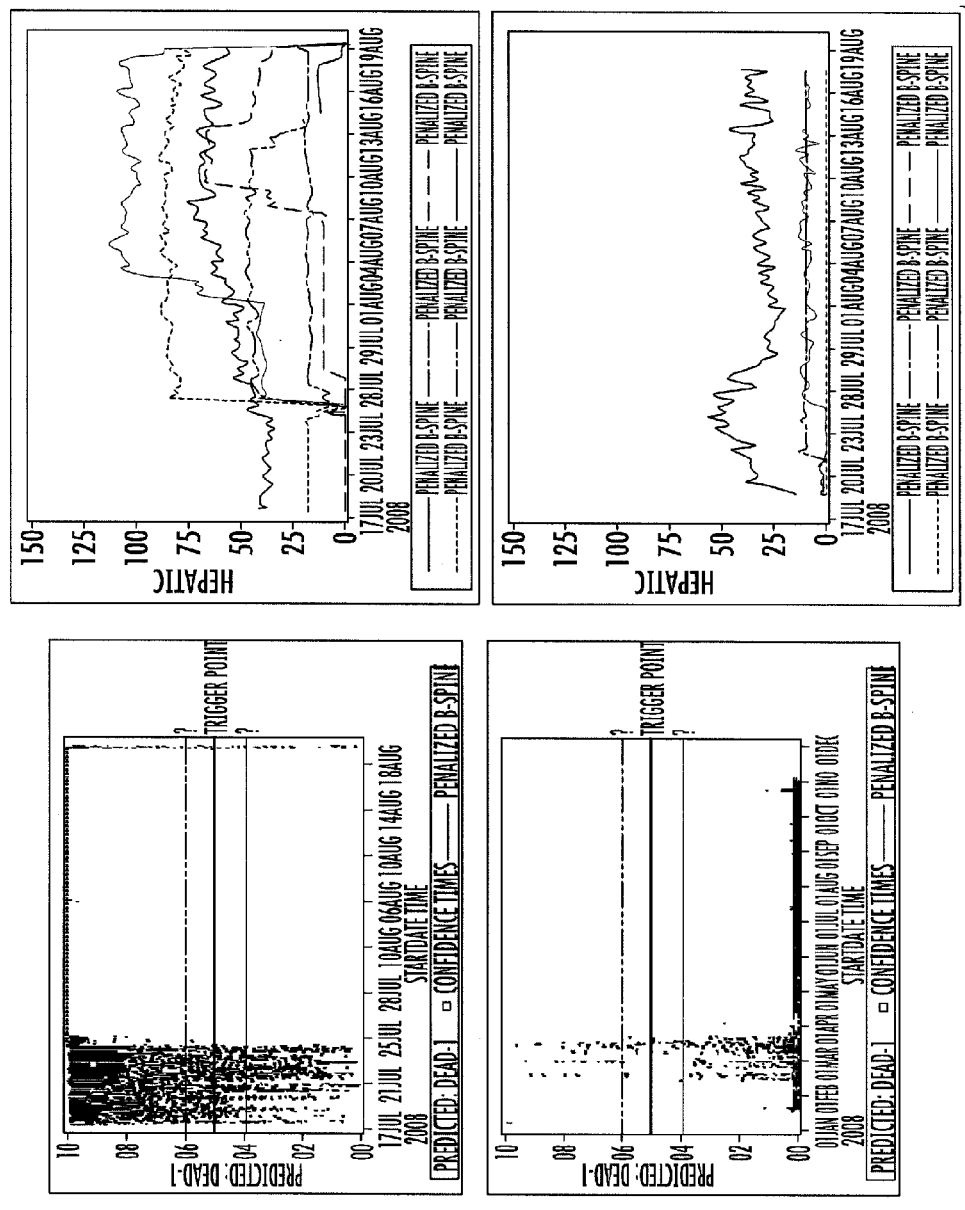
FIG. 17C includes graphs tracking each two minute score along with organ specific critical interval counts that may be generated by the system illustrated in FIG. 2 according to an embodiment of the subject matter described herein.

In the model, each factor represents a physiologic variable or combination of such variables. The "0" column represents beta weights for Live NICU patients while the "1" column represents beta weights for the dead NICU patients. In addition we have also produced PMML formatted scoring algorithms of the PICU and RR population. Abbreviated examples can be found for PICU in FIG. 18A and for RR in FIG. 18B. Although different critical intervals were identified for each patient population (NICU, PICU and RR), all follow the same reporting outlined in FIGS. 17A-17C. Complete versions of these models can be found in the above-referenced provisional patent application.

Improving ECG Signal Integrity: Pre-Processing of the ECG

Figure 19:
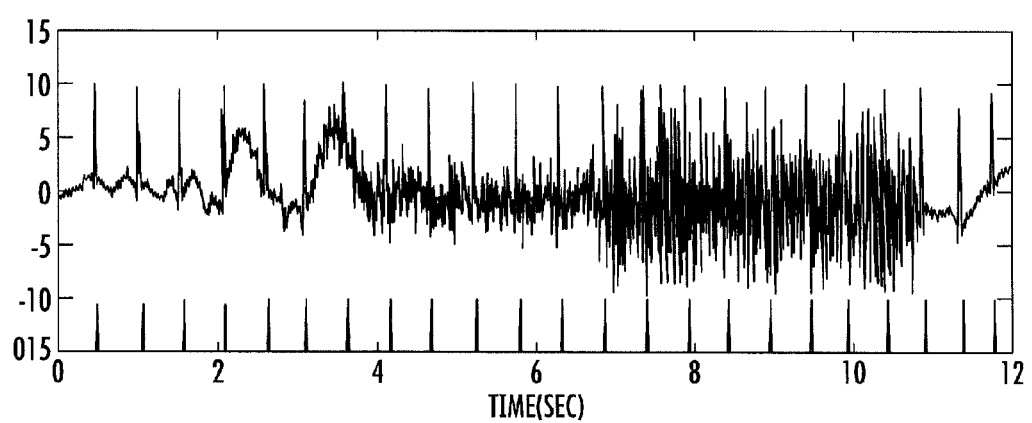
FIG. 19 is an example of an ECG signal with corruption that can be corrected using covariance according to an embodiment of the subject matter described herein.

According to another aspect of the subject matter described herein, the predictive accuracy of the models can be improved by pre-processing the ECG signal using a covariance function to lessen the effects of corruption in the ECG signal. Traditional methods of "R" wave detection of the ECG use a combination of signal conditioning, QRS detection and post-processing. QRS detection methods include amplitude threshold, first derivative threshold, moving average filters, high pass filters, cross correlation and others. Our approach is to use the covariance function (formula 1) in conjunction with statistical filtering to detect the "R" wave. We have found the covariance function is superior for QRS detection than standard cross-correlation or correlation coefficient function, since it removes baseline shifts and does not amplify other portions of the ECG other than the "R" wave. FIG. 19 is an ECG signal which has been corrupted: from second 2-4 with baseline shift due to motion artifact from deep breathing; from seconds 3-7 with moderate EMG artifacts due to a Valsalva maneuver; and from seconds 7-11 with intense pectoralis major muscle flexion.

$$C_{xy}(m) = \frac{1}{N} \sum_{n=0}^{N} (x(n) - \mu_x)(y(n+m) - \mu_y) \qquad \text{(formula 1)}$$

Using the covariance function (formula 1), the corruption can be removed. For example, when missing data is seen in ECG signals we "fill-in" using the correlation (covariance) with secondary sources (e.g., respiration) to estimate the missing ECG value. When high covariance(correlation) with secondary feeds exist, this approach has yielded significant value over a randomly assigned/blank values. In addition, when looking across multiple secondary feeds simultaneously we have reported more accurate estimates (fill-in value) then when just using single source.

Figure 20:
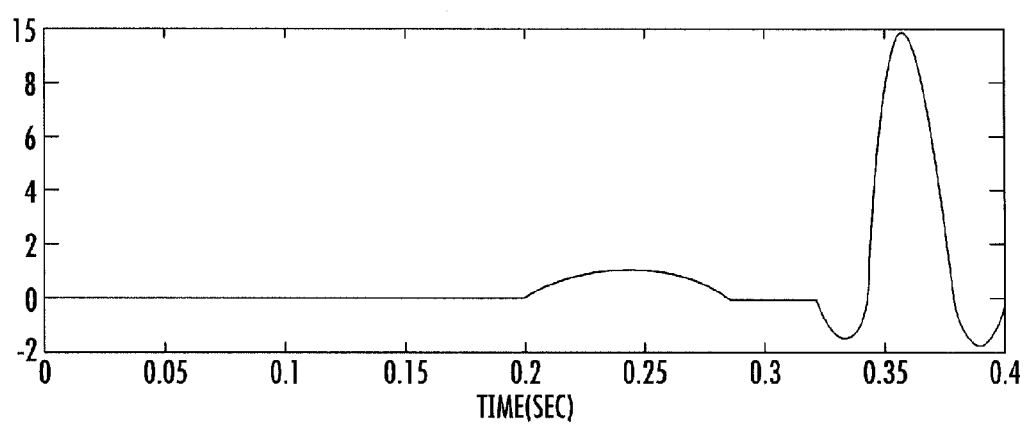
FIG. 20 is a graph of a QRS template.
Figure 21:
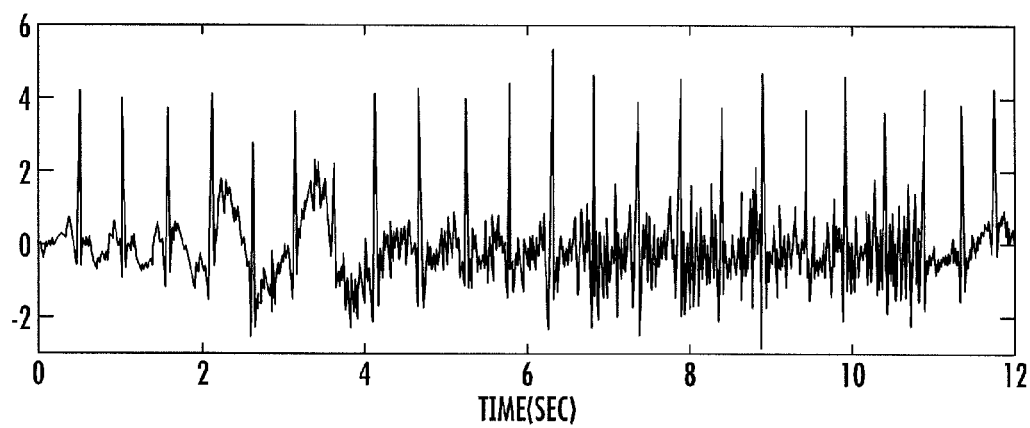
FIG. 21 is a graph of the covariance between the QRS template illustrated in FIG. 20 and the contaminated ECG signal illustrated in FIG. 19.

The covariance between the QRS template (FIG. 20) and the contaminated ECG (FIG. 19) is determined; with the output shown in FIG. 21.

Post Processing

Figure 22:
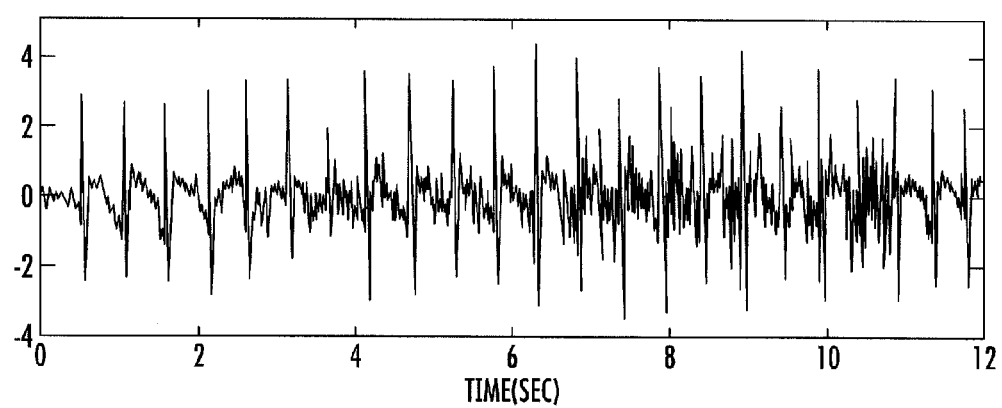
FIG. 22 is a graph of the output of a quadrature-mirrored, second order linear infinite impulse response filter use to remove baseline shifts in a QRS wave according to an embodiment of the subject matter described herein.

Other investigators have used finite impulse response (FIR), infinite impulse response (IIR) filters, adaptive filtering, cubic spline fitting, moving average filtering, median filtering, weighted average filtering, mathematical morphology and neural networks to aid in the identification of the QRS wave. We have implemented a quadrature-mirrored 2nd order linear high-pass IIR filter to remove the baseline shifts. The output is shown in FIG. 22.

Figure 23:
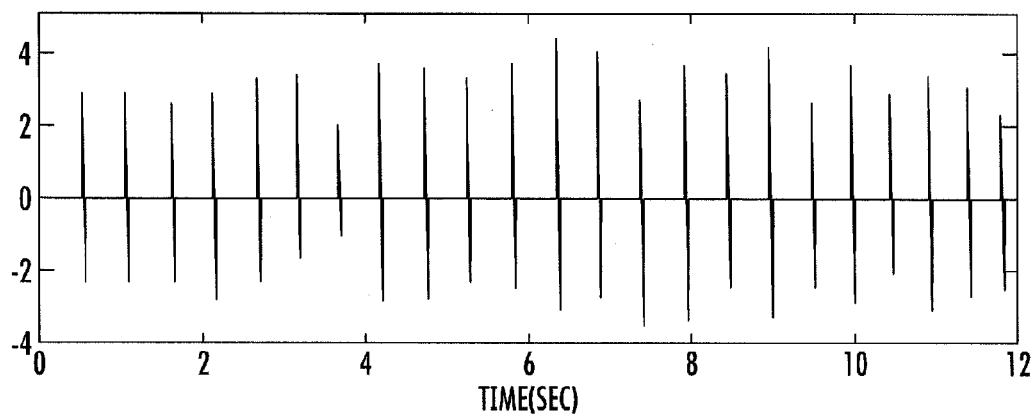
FIG. 23 is a graph of the R wave determined using a 2 sigma statistical filter according to an embodiment of the subject matter described herein.

The R wave was then distinguished using a 2-sigma statistical filter, followed by a low-pass discriminatory filter, as shown in FIG. 23.

Figure 24:
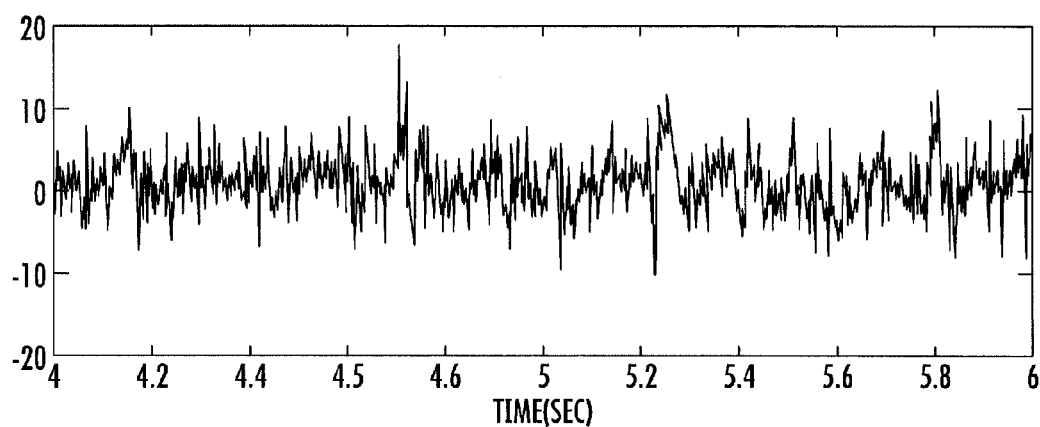
FIG. 24 is a graph of the output of a threshold and first derivative filter, which represents the ECG signal with contamination removed and after post-processing according to an embodiment of the subject matter described herein.

The output of the 2-sigma statistical filter is then applied to a Threshold and First Derivative filter, with the output of this final stage shown in FIG. 24. In this figure, the original contaminated ECG is displayed, with the output of the several filtering steps described above shown as binary values (1 or 0) along the bottom axis. The spikes (value 1) mark the occurrence of the "R" wave. The ECG signal in FIG. 24 represents a section of a worst-case scenario test signal with a SNR of 0.5 (−6.11 dB), which only occurs occasionally with poor sensor connectivity or during extreme patient activity (0.4 Hz—respiration, 3 Hz cardioballistic, 60 Hz—power line, 0-155 Hz, white noise). Applying this detection procedure, we are able to correctly detect the "R" wave on this ECG test signal at 92% sensitivity, with 20% false positives.

We have tested this "R" wave detection algorithm in a research study with 24 hr monitoring of sleep patients (20 subjects). While our current method is sufficient for ECG signal processing when off-line correction is appropriate, it is not sufficient for real-time continuous "R" wave detection for alarming, which must have very high real-time fidelity. High level Alarming for this condition must be prevented to achieve caregiver alertness through confidence in the alarm situation. We will improve our detection methodology to 99% detection with 5% false positives under this extreme condition of ECG contamination.

Alarming

Even following signal filtering and enhanced identification of "R" waves using cross-correlation of the ECG with QRS templates, waveform sections with missed beats or falsely marked "R" waves are inevitable, resulting in false alarms. We will employ a multi-tiered method for minimizing false alarms.

Heart Rate Alarms:

Three parallel records of heart period time-series will be derived following the initial signal conditioning and RR interval detection from the two ECG signals and the invasive or non-invasive pulse waveform obtained from the pulsed oximeter. Missing or false detections of the R-wave will be implied from unusually long (multiple of a single interval) or short (fractional) intervals. Paired comparisons will be made between these three data sets and improperly detected events will be corrected when they coincide with the expected interval. When a long segment of any of the three waveforms is false, a low-level alarm will be issued (poor sensor contact, high level noise, or sensor disconnect). When long segments (5 seconds) of all three waveforms are false, a high level alarm will be issued.

It will be understood that various details of the subject matter described herein may be changed without departing from the scope of the subject matter described herein. Furthermore, the foregoing description is for the purpose of illustration only, and not for the purpose of limitation.

What is claimed is:

1. A patient monitoring system for determining a risk of mortality of a patient located in a hospital, the apparatus comprising:
   a plurality of medical sensors connected to the patient each configured to measure a physiological parameter and transmit related physiological data of the patient, the plurality of medical sensors including:
      a blood pressure medical sensor configured to measure a blood pressure physiological parameter, and
      an electrocardiogram ("ECG") medical sensor configured to measure electrical activity of the patient's heart; and
   a patient monitor communicatively coupled to the plurality of medical sensors and a hospital system, the patient monitor including:
      a user interface configured to receive an identifier of the patient,
      a data collection module configured to periodically receive the physiological data from the plurality of medical sensors including blood pressure physiological data and ECG physiological data,
      a mortality risk engine operating a mortality risk scoring algorithm that is configured to determine the risk of mortality of the patient by:
         aggregating the physiological data from the medical sensors into regular defined time intervals related to when the physiological data was generated,
         applying a statistical filter to the physiological data from the medical sensors to at least one of remove signal corruption and adjust limits of a respective critical interval, and
         determining an ongoing risk of mortality of the patient, for each defined time interval, by
            (i) determining if a value of the blood pressure physiological data is included within a blood pressure critical interval, among a plurality of blood pressure critical intervals, each blood pressure critical interval including a first blood pressure beta weight that is correlated to a population of live patients that had blood pressure physiological data within the same blood pressure critical interval, and a second blood pressure beta weight that is correlated to a population of deceased patients that had blood pressure physiological data within the same blood pressure critical interval,
            (ii) responsive to determining that the blood pressure physiological data is included within the blood pressure critical interval, combining a first blood pressure occurrence value with the first blood pressure beta weight and a second blood pressure occurrence value with the second blood pressure beta weight, (iii) determining if a value of the ECG physiological data is included within an ECG critical interval, among a plurality of ECG critical intervals, each ECG critical interval including a first ECG beta weight that is correlated to a population of live patients that had ECG physiological data within the same ECG critical interval, and a second ECG beta weight that is correlated to a population of deceased patients that had ECG physiological data within the the same ECG critical interval, (iv) responsive to determining that the ECG physiological data is included within the ECG critical interval, combining a first ECG occurrence value with the first ECG beta weight and a second ECG occurrence value with the second ECG beta weight, (v) during the defined time interval, updating the first blood pressure occurrence value and the second blood pressure occurrence value if a current value of the blood pressure physiological data is included within one of the plurality of blood pressure critical intervals, and updating the first ECG occurrence value and the second ECG occurrence value if a current value of the ECG physiological data is included within one of the plurality of ECG critical intervals, and (vi) determining the ongoing risk of mortality for the patient using the first blood pressure occurrence value, the second blood pressure occurrence value, the first ECG occurrence value, and the second ECG occurrence value; and a display interface configured to display the ongoing risk of mortality in numerical or graphical form in conjunction with at least some of the physiological data from some of the plurality of medical sensors.

2. The patient monitoring system of claim 1, wherein the plurality of medical sensors include:

an oxygen saturation ($SPO_2$) medical sensor configured to measure arterial oxygen saturation of the patient; and a respiratory medical sensor configured to measure a breathing rate of the patient, wherein the data collection module is configured to receive oxygen saturation physiological data and respiratory rate physiological data.

3. The patient monitoring system of claim 1, wherein the mortality risk engine is configured to:

determine a time domain parameter, a frequency domain parameter, and a non-linear parameter for each defined time interval of the ECG physiological data; and score the time domain parameter, the frequency domain parameter, and the non-linear parameter to respective critical intervals, which when aggregated determine the ongoing risk of mortality.

4. The patient monitoring system of claim 2, wherein the mortality risk engine is configured to:

determine oxygen saturation occurrence values for the oxygen saturation physiological data using beta weights for at least one oxygen saturation critical interval;

determine respiratory rate occurrence values for the respiratory rate physiological data using beta weights for at least one respiratory rate critical interval; and determine the ongoing risk of mortality for the patient using in part the oxygen saturation occurrence values and the respiratory rate occurrence values.

5. The patient monitoring system of claim 1, wherein the mortality risk engine is configured to remove signal corruption from the ECG physiological data using a specific function for R-wave detection.

6. The patient monitoring system of claim 5, wherein the filtered ECG physiological data from the statistical filter is based on the R-wave.

7. The patient monitoring system of claim 1, wherein the patient monitor is configured to transmit at least one of an alert and an alarm responsive to the ongoing risk of mortality exceeding a predetermined threshold.

8. The patient monitoring system of claim 1, wherein the data collection module is configured to receive at least one of patient chart data and patient laboratory data associated with the patient.

9. The patient monitoring system of claim 8, wherein the mortality risk engine is configured to:

aggregate the at least one of the patient chart data and the patient laboratory data with the physiological data from the medical sensors; and determine the ongoing risk of mortality of the patient using the at least one of patient chart data and the patient laboratory data.

* * * * *